(12) United States Patent
Baichwal et al.

(10) Patent No.: US 9,278,076 B2
(45) Date of Patent: Mar. 8, 2016

(54) CHRONOTHERAPEUTIC DOSAGE FORMS

(75) Inventors: Anand R. Baichwal, Wappingers Falls, NY (US); Paul Woodcock, Brookfield, CT (US); Steve Labudzinski, Poughkeepsie, NY (US)

(73) Assignee: Endo Pharmaceuticals Inc., Malvern, PA (US)

( * ) Notice: Subject to any disclaimer, the term of this patent is extended or adjusted under 35 U.S.C. 154(b) by 660 days.

(21) Appl. No.: 12/380,642

(22) Filed: Mar. 2, 2009

(65) Prior Publication Data

US 2009/0169587 A1    Jul. 2, 2009

Related U.S. Application Data

(63) Continuation of application No. 10/943,711, filed on Sep. 17, 2004, now abandoned.

(60) Provisional application No. 60/504,037, filed on Sep. 19, 2003.

(51) Int. Cl.
*A61K 9/20* (2006.01)
*A61K 9/50* (2006.01)

(52) U.S. Cl.
CPC ............... *A61K 9/5036* (2013.01); *A61K 9/501* (2013.01); *A61K 9/2054* (2013.01)

(58) Field of Classification Search
None
See application file for complete search history.

(56) References Cited

U.S. PATENT DOCUMENTS

| | | | |
|---|---|---|---|
| 3,148,124 A * | 9/1964 | Gaunt | 424/468 |
| 5,811,388 A | 9/1998 | Friend et al. | |
| 5,858,412 A | 1/1999 | Staniforth et al. | |
| 6,046,277 A | 4/2000 | Kolter et al. | |
| 6,190,692 B1 | 2/2001 | Busetti et al. | |
| 6,228,398 B1 | 5/2001 | Devane et al. | |
| 6,500,459 B1 | 12/2002 | Chhabra et al. | |
| 2002/0028240 A1 * | 3/2002 | Sawada et al. | 424/472 |
| 2003/0082230 A1 * | 5/2003 | Baichwal et al. | 424/470 |

FOREIGN PATENT DOCUMENTS

| | | |
|---|---|---|
| EP | 0519099 | 12/1992 |
| EP | 05266862 | 2/1996 |
| EP | 1064938 A1 * | 1/2001 |
| WO | WO 02072033 A2 * | 9/2002 |

OTHER PUBLICATIONS

EP Supplementary Search Report for European Application No. 02721430.3 (2004).
Krishnaiah Ysr, S Satyanarayana, and Yv Rama Prasad. 1999. Studies of Guar Gum Compression-Coated 5-Aminosalicylic Acid Tablets for Colon-Specific Drug Delivery. Drug Development and Industrial Pharmacy.; 25(5): 651-657.

* cited by examiner

*Primary Examiner* — Susan Tran
(74) *Attorney, Agent, or Firm* — Davidson, Davidson & Kappel LLC

(57) ABSTRACT

A chronotherapeutic pharmaceutical formulation comprising a core containing an active agent (e.g., a drug) and a surfactant and a delayed release compression coating comprising a natural or synthetic gum applied onto the surface of the core.

20 Claims, No Drawings

CHRONOTHERAPEUTIC DOSAGE FORMS

This application is a continuation of U.S. patent application Ser. No. 10/943,711, filed Sep. 17, 2004 which claims the benefit of U.S. Provisional Patent Application No. 60/504,037, filed on Sep. 19, 2003, the disclosures of which are hereby incorporated by reference in its their entirety.

FIELD OF THE INVENTION

The present invention relates to a chronotherapeutic dosage form containing a therapeutically effective amount of a drug. The present invention is further related to methods of preparing such formulations, and to methods of treatment utilizing such formulations.

BACKGROUND OF THE INVENTION

Coordinating biological rhythms (chronobiology) with medical treatment is called chronotherapy. Chronotherapy takes into consideration a person's biological rhythms in determining the timing—and sometimes the amount—of medication to optimize desired effects of a drug(s) and minimize the undesired effects. The synchronization of medication levels to the biological rhythms of disease activity is playing an increasing role in the management of common cardiovascular conditions such as hypertension, elevated cholesterol, angina, stroke and ischemic heart disease, according to experts in this new and ever-expanding field. For example, in humans, at 1 am post-surgical death is most likely; at 2 am peptic ulcers flare up; at 3 am blood pressure bottoms out; at 4 am asthma is at its worst. When one wakes up, hay fever is at its most tormenting, and in the morning hours, as ones blood pressure rises to meet the day, one is most likely to suffer a heart attack or stroke. Rheumatoid arthritis improves through the day, but osteoarthritis grows worse. Alcohol is least toxic to the body at around 5 pm: cocktail hour.

The first application of chronotherapy, in the 1960s, was a synthetic corticosterdid tablet (Medrol, Upjohn). Clinicians found that when used in the morning, the drug was more effective and caused fewer adverse reactions. Another example of a commercial product employing chronotherapy is the bronchodilator, Uniphyl®, a long-acting theophylline preparation manufactured by Purdue Frederick (approved by the FDA in 1989). Taken once a day at dinner to control night-time asthma symptoms. Uniphyl causes theophylline blood levels to reach their peak and improve lung function during the difficult morning hours.

Oral controlled release delivery systems may also be capable of passing over the entire tract of the small intestine, including the duodenum, jejunum, and ileum, so that the active ingredients can be released directly in the colon, if such site specific delivery is desired. One means of accomplishing this is by providing a coating surrounding the active pharmaceutical formulation core so as to preserve the integrity of the formulation while it is passing through the gastric tract. The high acidity of the gastric tract and presence of proteolytic and other enzymes therein generates a highly digestive environment that readily disintegrates pharmaceutical formulations that do not possess some type of gastro-resistance protection. This disintegration would typically have a detrimental effect upon the sustained release of the active agent. Such coated pharmaceutical formulations, in addition to slowing the release rate of the active agent contained within the core of the tablet, can also effectuate a delay in the release of the active ingredient for a desired period of time such that the dissolution of the active drug core can be delayed.

Examples of coated pharmaceutical delivery systems for delayed release can be found in U.S. Pat. No. 4,863,742 (Panoz et al.) and U.S. Pat. No. 5,891,474 (Busetti et al.), as well as in European Patent Applications Nos. 366 621, 572 942 and 629 398. In the delayed release tablets described in each of these references, the therapeutically active drug core is coated with at least one and potentially several layers of coating, wherein the layers of coating have a direct effect upon the timed release of the active drug within the tablet core into the system of the patient.

PCT publications WO 02/072033 and WO 02/072034, the disclosures of which are hereby incorporated by reference, disclose chronotherapeutic pharmaceutical formulations comprising a core containing an active agent (e.g., a drug) and a delayed release compression coating comprising a natural or synthetic gum applied onto the surface of the core.

It is considered desirable by those skilled in the art to provide an oral controlled release delivery system that is adaptable to deliver a drug(s) such that release rates and drug plasma profiles can be matched to physiological and chronotherapeutic requirements.

OBJECTS AND SUMMARY OF THE INVENTION

It is an object of the present invention to provide an oral pharmaceutical dosage form that releases a drug(s) into the body of a patient at a predetermined time after oral ingestion of the dosage form by the patient.

It is a further object of the present invention to provide an oral pharmaceutical dosage form that provides a delayed release of a drug(s) into the gastrointestinal tract of a patient at a predetermined time after oral ingestion of the dosage form.

It is a further object of certain embodiments of the present invention to provide an oral pharmaceutical dosage form having a core containing drug, the core being compression coated with a coating that provides a delayed release of the drug from the dosage form after the dosage form is orally administered to a patient.

It is a further object of certain embodiments of the present invention to provide an oral pharmaceutical dosage form having a drug-containing core that is compression coated with a coating which provides a delayed release of the drug when the dosage form is orally administered to a patient.

It is a further object of certain embodiments of the present invention to provide a dosage form which allows time-specific dosing form a wide variety of diseases.

It is a further object of certain embodiments of the present invention to provide a dosage form which allows time-specific dosing for arthritis, high blood pressure, or asthma, which are typically more symptomatic in the early morning corresponding to circadian rhythms.

It is a further object of certain embodiments of the present invention to provide a dosage form which provides a delayed release of drug from the dosage form, followed by a sustained release of the drug thereafter as the dosage form travels through the gastrointestinal tract.

It is a further object of certain embodiments of the present invention to provide a compression coated dosage form having an immediate release layer of a drug(s) overcoating a compression coated core which provides a delayed release of the same or different drug(s) from the dosage form; the core optionally providing a sustained release of the drug thereafter as the dosage form travels through the gastrointestinal tract.

It is a further object of certain embodiments of the present invention to provide an oral dosage form which provides site-specific deliver of drug (e.g., to the colon).

It is a further object of certain embodiments of the present invention to develop an oral dosage form which provides programmed release of drug.

It is a further object of certain embodiments of the present invention to develop an oral dosage form which provides pulsatile release of drug.

In accordance with the above-mentioned objects of the invention, the present invention is directed in part to an oral dosage form which comprises a core comprising a therapeutically effective amount of a drug, a pharmaceutically acceptable surfactant and other optional pharmaceutically acceptable excipients, and a compress ion coating material applied to the tore, the compression coating having a delayed release material; comprising one or more natural or synthetic, gums which are compression coated onto its surface such that the release of the drug from the dosage form is delayed for a desired time period after oral administration of the dosage form to a mammal (e.g., human patient).

In certain preferred embodiments, the compression coating comprises a mixture (e.g., matrix) of xanthan gum, locust bean gum, and a pharmaceutically acceptable saccharide, e.g., a monosaccharide, a disaccharide, a polyhydric alcohol, or a combination of any of the foregoing. In certain preferred embodiments, the core is an immediate release core comprising the drug and a pharmaceutically acceptable surfactant together with one or more pharmaceutically acceptable excipients.

The invention is further directed in part to a delayed release oral solid dosage form comprising a core comprising a therapeutically effective amount of a drug(s) and a pharmaceutically acceptable surfactant, and a delayed release material compression coated onto said core, the delayed release material comprising one or more natural or synthetic gums, the compression coating delaying the release of said drug from said dosage form for a period of time from about 2 to about 18 hours after exposure of the dosage form to an aqueous solution.

The invention is further directed in part to a delayed release oral solid dosage form comprising a core comprising a therapeutically effective amount of a drug(s) and a pharmaceutically acceptable surfactant, and an agglomerated delayed release material compression coated onto the core, the agglomerated delayed release material comprising a gum selected from, e.g., a homopolysaccharide, a heteropolysaccharide, and a mixture of a homopolysaccharide and a heteropolysaccharide, together with a pharmaceutically acceptable excipient, the compression coating delaying the release of said drug from the dosage form for a predetermined period of time after exposure of the dosage form to an aqueous solution.

The invention is further directed in part to a delayed release oral solid dosage form comprising a core comprising a therapeutically effective amount of a drug(s), a pharmaceutically acceptable surfactant and a disintegrant, and a delayed release material compression-coated onto the core, said delayed release material comprising one or more natural or synthetic gums, said compression coating delaying the release of the drug from the dosage form for a predetermined period of time after exposure of the dosage form to an aqueous solution, the disintegrant and surfactant being included in the core in an amount effective to cause the release of at least about 50 percent of the drug into said aqueous solution within one hour after said predetermined period of time.

The invention is further directed in part to a delayed release oral solid tablet, comprising a tablet core comprising a therapeutically effective amount of a drug and a pharmaceutically acceptable surfactant, and a delayed release material compression coated onto the core, the delayed release material comprising one or more natural or synthetic gums, the gums comprising from about 6.5 percent to about 83 percent of the tablet by weight, said compression coating delaying the release of said drug from the dosage form for a period of time from about 2 to about 18 hours after exposure of the dosage form to an aqueous solution.

The invention is further directed to a chronotherapeutic, delayed release oral solid dosage form for low dose drugs, comprising a core comprising from about 0.01 mg to about 40 mg of a drug and a pharmaceutically acceptable surfactant, and a delayed release material compression coated onto the core, the delayed release material comprising one or more natural or synthetic gums, the compression coating comprising from about 75 to about 94 percent by weight of the oral solid dosage form, and the ratio of the core to gum in the compression coating being from about 1:0.37 to about 1:5, by weight the compression coating delaying the release of the drug from the dosage form for a period of time from about 2 to about 18 hours after exposure of the dosage form to an aqueous solution.

The invention is further directed in part to a chronotherapeutic delayed release oral solid dosage form for a relatively high dose drug, comprising a core comprising from about 41 mg to about 300 mg of a drug, and a delayed release material compression coated onto the core, the delayed release material comprising one or more natural or synthetic gums, the ratio of the core to gum in the compression coating being from about 1:0.3 to about 1:3, by weight, the total weight of the oral solid dosage form being from about 500 mg to about 1500 mg, the compression coating delaying the release of the drug from the dosage form for a period of time from about 2 to about 18 hours after exposure of the dosage form to an aqueous solution.

The invention is further directed in part to a method of preparing a chronotherapeutic oral solid dosage form of a drug, comprising preparing a core comprising a therapeutically effective amount of a drug(s), a pharmaceutically acceptable surfactant, and from about 5 to about 20% disintegrant, by weight of the core, preparing a granulate of a delayed release material comprising one or more natural or synthetic gums, compression coating the granulate onto said core, the compression coating delaying the release of said drug from the dosage form until after a period of time from about 2 to about 18 hours after exposure of the dosage form to an aqueous solution. In certain preferred embodiments, the method further comprises preparing the granulate of delayed release material by wet granulating one or more natural or synthetic gums together with at least one pharmaceutically acceptable excipient, and drying the resultant granulate to obtain agglomerated particles of the delayed release material. In certain embodiments the method further comprises granulating the drug, the pharmaceutically acceptable surfactant, the disintegrant, and a pharmaceutically acceptable inert diluent prior to the compression coating step.

In certain embodiments, the surfactant is in an effective amount to facilitate the release of the drug from the dosage form upon exposure of the dosage form to an aqueous solution. In certain preferred embodiments, the surfactant is included in an amount that facilitates the immediate release of the drug from the core of the dosage form upon exposure of the dosage form to an aqueous solution. For example, in certain embodiments, after the dosage form is exposed to an aqueous solution, the coating of the dosage form delays the release of the drug from the dosage form by delaying the exposure of the core to the aqueous solution, after the aqueous solution is exposed to the core, the inclusion of the surfactant in the core promotes the release of the drug from the core (e.g., by promoting dissolution of the drug the into the aqueous solution).

In certain preferred embodiments, the inclusion of the surfactant in the core of the dosage form facilitates the complete release of the drug from the dosage form in less than 4 hours after initial release, preferably in less than 3 hours after initial release, more preferably in less 2 hours after initial release, and most preferably in less than 1 hour after initial release.

In certain preferred embodiments, the surfactant for use in the core of the dosage forms of the present invention include pharmaceutically acceptable anionic surfactants, cationic surfactants, amphoteric (amphipathic/amphophilic) surfactants, and non-ionic surfactants. Suitable pharmaceutically acceptable anionic surfactants include, for example, monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates (including sodium lauryl sulfate (SLS)), ethoxylated alkyl sulfates, ester linked sulfonates (including docusate sodium or dioctyl sodium succinate (DSS)), alpha olefin sulfonates, and phosphated ethoxylated alcohols.

Suitable pharmaceutically acceptable cationic surfactants include, for example, monoalkyl quaternary ammonium salts, dialkyl-quaternary ammonium compounds, amidoamines, and aminimides.

Suitable pharmaceutically acceptable amphoteric (amphipathic/amphophilic) surfactants, include, for example, N-substituted alkyl amides, N-alkyl betaines, sulfobetaines, and N-alkyl β-aminoproprionates.

Other suitable surfactants for use in conjunction with the present invention include polyethyleneglycols as esters or ethers. Examples include polyethoxylated castor oil, polyethoxylated hydrogenated castor oil, polyethoxylated fatty acid from castor oil or polyethoxylated fatty acid from hydrogenated castor oil. Commercially available surfactants that can be used are known under trade names Cremophor, Myrj, Polyoxyl 40 stearate, Emerest 2675, Lipal 395 and PEG 3350.

In certain preferred embodiments, combinations of the aforementioned surfactants may be used in the cores of the dosage forms of the present invention.

In certain embodiments the surfactant in not sodium lauryl sulfate. In certain embodiment, when one surfactant is included in the core, the surfactant is not sodium lauryl sulfate.

In certain preferred embodiments, the surfactant in the core is included in an amount of from about 1 to about 20% by weight of the dosage form.

In certain preferred embodiments, the disintegrant: is a superdisintegrant incorporated in the core in an amount effective to cause the release of at least about 50 percent of the drug into the aqueous solution within one hour upon completion of the time period for delayed release.

The invention is further directed to methods of treatment utilizing the formulations disclosed herein.

In certain embodiments, the oral dosage form provides a lag time (delayed release of drug) from about 2 to about 18 hours, after oral administration to, e.g., a human subject or patient.

In certain preferred embodiments, the oral dosage form releases at least about 50 percent of the drug(s) contained in the core within about one hour, and preferably at least about 80 percent of the drug(s) contained in the core within about one or two hours, after the end of the lag time provided by the compression coating.

In certain embodiments, the oral dosage form of the invention provides a lag time of from about 5 to about 8 hours with a full release by about 8 to about 12 hours, after oral administration, e.g., to a human patient.

In certain preferred embodiments, the oral dosage form provides a lag time of about 6 to about 7 hours with full release by about 8 to about 9 hours, after oral administration of the dosage form.

In certain other preferred embodiments, the oral dosage form provides a lag time of about 6 to about 7 hours, followed by full release of the drug by about 7 to about 8 hours after oral administration.

In yet other embodiments, the formulation provides a lag time from about 9 to about 12 hours, with full release by about 11 to about 13 hours after oral administration, preferably a lag time of about 10 to about 11 hours followed by full release at about 11 to about 12 hours after oral administration of the dosage form.

In yet other embodiments, the formulation provides a lag time of, e.g., about 3-12 hours, with full release of the drug from the dosage form within about 24 hours, or (alternatively) after 24 hours.

By "delayed release" it is meant for purposes of the present invention that the release of the drug is delayed and the drug is contained in the dosage form not substantially released from the formulation until after a certain period of time, e.g., such that the drug is not released into the bloodstream of the patient immediately upon ingestion by the patient of the tablet but rather only after a specific period of time, e.g., a 4 hour to a 9 hour delay. For purposes of the present invention, delayed release is synonymous with "timed delay" or a release of drug after a lag time, or a programmed release.

By "sustained release" it is meant for purposes of the present invention that, once the drug is released from the formulation, it is released at a controlled rate such that therapeutically beneficial blood levels (but below toxic levels) of the medicament are maintained over an extended period of time from the start of drug release, e.g., providing a release over a time period, e.g., from about 4 to about 24 hours from the point of drug release after the lag time, onward.

The term "Cmax" is meant for purposes of the present invention to mean the maximum plasma concentration of a medicament achieved after single dose administration of a dosage form in accordance with the present invention.

The term "Tmax" is meant for purposes of the present invention to mean the elapsed time from administration of a dosage form to the time the Cmax of the medicament is achieved.

The term "mean" for purposes of the present invention, when used to define a pharmacokinetic value (e.g., Tmax) represents the arithmetic mean value measured across a patient population. The term "environmental fluid" is meant for purposes of the present invention to encompass, e.g., an aqueous solution (e.g., an in-vitro dissolution bath) or gastrointestinal fluid.

The term USP apparatus type III used herein is described e.g., in the United States Pharmacopeia XXV (2002).

DETAILED DESCRIPTION OF THE INVENTION

The present invention may be employed to achieve the time-delayed release of a pharmaceutically active agent, and in certain embodiments to provide a controlled-release pharmaceutical formulation for pharmaceutically active agents that are desirously delivered over a predetermined period of time. The formulations of the present invention provide the time-delayed release of a pharmaceutically active agent and may be useful for the treatment of conditions that are desirously treated through time-delayed pharmaceutical agent delivery mechanisms. For example, the formulations of the present invention are useful for the treatment of morning pathologies, i.e., conditions, diseases, or other illnesses, such as arthritis, hypertension and asthma, the symptoms of which are generally more acute in the morning as the patient awakens from sleep. These conditions may be treated by administering the time-delayed release formulation according to the present invention to the patient prior to sleeping, such that the delivery of the drug is achieved at about the time the patient awakens, or preferably the drug has been delivered from the dosage form (and absorbed from the gastrointestinal tract) to an extent that it has achieved a therapeutic effect, thereby alleviating the symptoms of the morning pathology.

The formulations of the present invention comprise a core comprising the active agent (e.g., drug) and a compression coating over the core that comprises one or more natural or synthetic pharmaceutically acceptable gums. In certain especially preferred embodiments, the compression coating comprises a combination of a heteropolysaccharide gum (e.g., xanthan gum) and a homopolysaccharide gum (e.g., locust bean gum), together with a pharmaceutically acceptable saccharide (e.g., lactose, dextrose, mannitol, etc.). In certain preferred embodiments, the gum(s) are wet granulated together with the optional saccharide(s) to form agglomerated particles comprising a mixture of, e.g., xanthan gum, locust bean gum and dextrose.

The goal of the compression coating of the present invention is to delay the release of the active agent, for a predetermined period of time, referred to in the art as a "lag time." In certain embodiments, the release of the active agent is delayed for, or has a lag time of, about 2 to about 18 hours after administration of the dosage form.

The core comprising the active agent can be formulated for either immediate release or sustained release of the active agent. Formulations for both immediate release and sustained release of active agents are well known to those skilled in the art. In accordance with certain embodiments of the present invention, it has been found that the inclusion of a surfactant in the core provides for an improved immediate release of the active agent.

In the present invention, when the core comprising the drug is formulated for immediate release, the core can be prepared by any suitable tableting technique known to those skilled in the art. For example, the pharmaceutically active agent may be admixed with excipient(s) and formed into a tablet core using a conventional tableting press or using conventional wet granulation techniques. According to certain preferred embodiments of the present invention, ingredients for the core are dry blended in a V-blender and compressed on a rotary tablet press into tablet cores. Alternatively, in certain embodiments, the ingredients for the core can be wet granulated, dried and thereafter compressed into tablet cores. Preferably, the core should be compressed to a degree of hardness such that they do not chip or come apart during further processing, such as during the coating process. In certain embodiments, the cores can be compressed to 50 mg weight and 2 to 8, preferably 4 to 8, most preferably 4-5 kP hardness. In addition, tablet core size should range from ⅛ inch to ⅝ inch, preferably from ⅛ inch to ½ inch, more preferably from 3/16 inch to ¼ inch.

In certain embodiments, wherein the core is manufactured without a wet granulation step, and the final mixture is to be compressed into a tablet core, all or part of the excipient in the core may comprise a pre-manufactured direct compression diluent. Examples of such pre-manufactured direct compression diluents include Emcocel® (microcrystalline cellulose, N.F.) and Emdex® (dextrates, N.F.), which are commercially available from JRS Pharma LP, Patterson, N.Y., and Tab-Fine® (a number of direct-compression sugars including sucrose, fructose and dextrose). Other direct compression diluents include anhydrous lactose (Lactose N.F., anhydrous direct tableting) from Sheffield Chemical, Union, N.J. 07083; Elcems® G-250 (powdered cellulose, N.F.) from Degussa, D-600 Frankfurt (Main) Germany; Fast-Flo Lactose® (Lactose, N.F., spray dried) from Foremost Whey Products, Banaboo, Wis. 53913; Maltrin® (Agglomerated maltodextrin) from Grain Processing Corp., Muscatine, Iowa 52761; Neosorb 60® (Sorbitol, N.F., direct-compression from Roquet Corp., 645 5th Ave., New York, N.Y. 10022; Nu-Tab® (Compressible sugar, N.F.) from Ingredient Technology, Inc., Pennsauken, N.J. 08110; Polyplasdone XL® (Crospovidone, N.F., cross-linked polyvinylpyrrolidone) from GAF Corp., New York, N.Y. 10020; Primojel® (Sodium starch glycolate, N.F., carboxymethyl starch) from Generichem, Corp., Little Falls, N.J. 07424; Solka Floc® (Cellulose floc); Spray-dried Lactose® (Lactose N.F., spray dried) from Foremost Whey Products, Baraboo, Wis. 53913 and DMV Corp., Vehgel, Holland; and Sta-Rx 15000® (Starch 1500) (Pregelatinized starch, N.F., compressible) from Colorcon, Inc., West Point, Pa. 19486. In certain embodiments of the present invention, the directly compressible inert diluent which is used in the core of the present invention is an augmented microcrystalline cellulose as disclosed in U.S. Pat. No. 5,585,115, issued Dec. 17, 1996, and entitled "PHARMACEUTICAL EXCIPIENT HAVING IMPROVED COMPRESSIBILITY", hereby incorporated by reference in its entirety. The augmented microcrystalline cellulose described therein is commercially available under the tradename Prosolv® from JRS Pharma.

Alternatively, in certain embodiments, the core comprising the active agent can be formulated as a sustained release core for the sustained release of the active agent. When the core comprising the active agent is formulated for sustained release, the core can be prepared in a number of ways known in the art. For example, the active agent can be incorporated in a sustained release matrix and thereafter compressed into a core, or a sustained release material can be coated onto the immediate release core to provide for the sustained release of the active agent, or a combination of the compressed sustained release matrix and sustained release coating on the core can be used. Additionally, spheroids comprising the active agent, or multiparticulates with sustained release coatings and comprising the active agent, may be compressed with optional binders and other excipients into a sustained release core.

When the core of the present invention comprises a sustained release matrix, the matrix formulations are generally prepared using standard techniques well known in the art. Typically, they are prepared by dry blending a sustained release material, diluent, active agent, and optional other excipients followed by granulating the mixture until proper granulation is obtained. The granulation is done by methods known in the art. Typically with a wet granulation, the wet granules are dried in a fluid bed dryer, sifted and ground to appropriate size. Lubricating agents are mixed with the dried granulation to obtain the final core formulation.

In our U.S. Pat. Nos. 4,994,276; 5,128,143; 5,135,757; 5,455,046; 5,512,297; 5,554,387; 5,667,801; 5,846,563; 5,773,025; 6,048,548; 5,662,933; 5,958,456; 5,472,711; 5,670,168; and 6,039,980, all of which are hereby incorporated by reference, we reported, that a controlled release excipient that is comprised of a gelling agent such as synergistic hetero disperse polysaccharides (e.g., a heteropolysaccharide such as xanthan gum) preferably in combination with a polysaccharide gum capable of cross-linking with the heteropolysaccharide (e.g., locust bean gum) is capable of processing into oral solid dosage forms using either direct compression, following addition of drug and lubricant powder, conventional wet granulation, or a combination of the two. These systems (controlled release excipients) are commercially available under the trade name TIMERx® from Penwest Pharmaceuticals Co., Patterson, N.Y., which is the assignee of the present invention.

In certain embodiments of the present invention, wherein the core provides for the sustained release of the active agent, the core comprises a sustained release matrix such as those disclosed in our foregoing patents. For example, in certain embodiments of the present invention, in addition to the active agent, the core comprises a sustained release excipient comprising a gelling agent comprising a heteropolysaccharide gum and a homopolysaccharide gum capable of cross-linking said heteropolysaccharide gum when exposed to an environmental fluid, and an inert pharmaceutical diluent. Preferably, the ratio of the heteropolysaccharide gum to the homopolysaccharide gum is from about 1:3 to about 3:1, and the ratio of active agent to gelling agent is preferably from about 1:3 to about 1:8. The resulting core preferably provides a therapeutically effective blood level of the active agent for at least about 4 hours, and in certain preferred embodiments, for about 24 hours. In certain preferred embodiments, the sustained release excipient further comprises an effective amount of a pharmaceutically acceptable ionizable gel strength enhancing agent, such as those described hereinafter, to provide a sustained release of the active when the core is exposed to an environmental fluid. The sustained release excipient (with or without the optional ionizable gel strength enhancing agent) may be further modified by incorporation of a hydrophobic material which slows the hydration of the gums without disrupting the hydrophilic matrix. In addition, in certain embodiments, the sustained release excipient can be modified to provide for bi- or multi-phasic release profiles of the active agent by the inclusion of a pharmaceutically acceptable surfactant or wetting agent in the core. Alternatively, the sustained release excipient comprises only one of the aforementioned gums. In yet other embodiments, the sustained release excipient comprises a different pharmaceutically acceptable gum.

In addition to the above, other sustained release materials may be used for the sustained release matrix cores of the inventive formulations. A non-limiting list of suitable sustained-release materials which may be included in a sustained-release matrix according to the present invention include hydrophilic and/or hydrophobic materials such, as sustained release polymers gums, acrylic resins, protein derived materials, waxes, shellac, and oils such as hydrogenated castor oil, hydrogenated vegetable oil. Preferred sustained-release polymers include alkylcelluloses such as ethylcellulose, acrylic and methacrylic acid polymers and copolymers; and cellulose ethers, especially hydroxyalkylcelluloses (especially hydroxypropylmethylcellulose) and carboxyalkylcelluloses. Preferred waxes include for example natural and synthetic waxes, fatty acids, fatty alcohols, and mixtures of the same (e.g., beeswax, carnauba wax, stearic acid and stearyl alcohol). Certain embodiments utilize mixtures of any of the foregoing sustained release materials in the matrix of the core. However, any pharmaceutically acceptable hydrophobic or hydrophilic sustained-release material which is capable of imparting sustained-release of the active agent may be used in accordance with the present invention.

Alternatively, in certain embodiments of the present invention, the core may be formulated to provide for the sustained release of the active agent through the use of an immediate release core (as previously described) with a sufficient amount of a hydrophobic coating to provide for the sustained release of the active agent from the immediate release core. The hydrophobic coating may be applied to the core using methods and techniques known to those skilled in the art. Examples of suitable coating devices include fluid bed coaters, pan coaters, etc. Examples of hydrophobic materials which may be used in such hydrophobic coatings include for example, alkylcelluloses (e.g., ethylcellulose), copolymers of acrylic and methacrylic acid esters, waxes, shellac, zein, hydrogenated vegetable oil, mixtures thereof, and the like.

Additionally, the cores may be formulated for sustained release of the active agent by using a combination of the sustained release matrix and sustained release coating. The sustained release cores (e.g., sustained release matrix, sustained release coated, or combination thereof), and the immediate release cores, may also contain suitable quantities of additional excipients, e.g., lubricants, binders, granulating aids, diluents, colorants, flavorants and glidants which are conventional in the pharmaceutical art.

Specific examples of pharmaceutically acceptable diluents and excipients that may be used in formulating the cores are described in the *Handbook of Pharmaceutical Excipients*, American Pharmaceutical Association (1986), incorporated by reference herein.

The cores of the present invention, particularly the immediate release cores, further include a surfactant, which contributes to the release of the active agent from the dosage form. Surfactants for use in the present invention include pharmaceutically acceptable anionic surfactants, cationic surfactants, amphoteric (amphipathic/amphophilic) surfactants, and non-ionic surfactants. Suitable pharmaceutically acceptable anionic surfactants include, for example, monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates (including sodium lauryl sulfate (SLS)), ethoxylated alkyl sulfates, ester linked sulfonates (including docusate sodium or dioctyl sodium succinate (DSS)), alpha olefin sulfonates, and phosphated ethoxylated alcohols.

Suitable pharmaceutically acceptable cationic surfactants include, for example, monoalkyl quaternary ammonium salts, dialkyl quaternary ammonium compounds, amidoamines, and aminimides.

Suitable pharmaceutically acceptable amphoteric (amphipathic/amphophilic) surfactants, include, for example, N-substituted alkyl amides, N-alkyl betaines, sulfobetaines and N-alkyl 6-aminoproprionates.

Other suitable surfactants for use in conjunction with the present invention include polyethyleneglycols, esters or ethers thereof. Examples include polyethoxylated castor oil, polyethoxylated hydrogenated castor oil, polyethoxylated fatty acid from castor oil or polyethoxylated fatty acid from hydrogenated castor oil. Commercially available surfactants that can be used are known under trade names Cremophor, Myrj, Polyoxyl 40 stearate, Emerest 2675, Lipal 395 and PEG 3350.

In certain preferred embodiments, certain combinations of the aforementioned surfactants are used in the cores of the dosage forms of the present invention. In certain preferred embodiment, the surfactant includes the combination of two or more surfactants (e.g., PEG and sodium lauryl sulfate). In certain embodiments in which the therapeutic active drug is formulated for immediate release, when no surfactant is present, a controlled profile may be produced.

In certain embodiments, the one or more surfactants included in the core is in an amount of from about 5 to about 50 percent, preferably from about 10 to about 30 percent, by weight of the core. In terms of whole tablet weight (e.g., core plus compression coating), the one or more surfactant(s) in the core are included in an amount of from about 1 to about 20 percent, preferably from about 2 to about 10 percent, by weight of the tablet (entire formulation).

In certain preferred embodiments, the oral dosage form includes one or more disintegrants preferably incorporated in the core. When such an agent is included in the core, the rate of release of drug (after the initial delay caused by the compression coating) is an immediate pulse effect. In certain embodiments, when no disintegrant is present, a controlled profile may be produced. Suitable disintegrants are known to those skilled in the art, and include for example sodium starch glycolate (commercially available as Explotab® from JRS Pharma LP).

The mechanism of disintegration is based on swelling, wicking, and deformation of the disintegrants. When a compressed tablet is placed in aqueous solution, water can be quickly absorbed, and the swelling of the disintegrant breaks apart tablets quickly. In one embodiment in which the therapeutic active drug is formulated for immediate release, when a disintegrant is present in the core of the tablet, the rate of release of the active agent is an immediate pulse effect. In certain embodiments in which the therapeutic active drug is formulated for immediate release, when no disintegrant is present, a controlled profile may be produced.

Examples of such disintegrants for use in the present invention include, for example, starch, veegum, crospovidone, cellulose, kaolin, microcrystalline cellulose (e.g., Avicel PH101 & PH102), crosslinked polyvinyl pyrrolidone (e.g., Kolliddn CL), and mixtures thereof. In certain preferred embodiments, the disintegrant is a superdisintegrant, such as, for example, croscarmellose sodium, crospovidone, crosslinked carboxy methyl cellulose, sodium starch glycolate, and mixtures thereof. Superdisintegrants can be incorporated at lower levels than regular disintegrants to increase the water content. Some brand named superdisintegrants for use in the present invention include, Ac-Di-Solo, Primojel®, Explotab®, and Crospovidone®.

In certain embodiments, the core of the present invention includes a wicking agent in addition to or as an alternative to a disintegrant. Wicking agents such as those materials already mentioned as disintegrants (e.g. microcrystalline cellulose) may be included if necessary to enhance the speed of water uptake. Other materials suitable for acting as wicking agents include, but are not limited to, colloidal silicon dioxide, kaolin, titanium dioxide, fumed silicon dioxide, alumina, niacinamide, sodium lauryl sulfate, low molecular weight polyvinyl pyrrolidone, m-pyrol, bentonite, magnesium aluminum silicate, polyester, polyethylene, mixtures thereof, and the like.

In certain embodiments, the one or more disintegrant(s) in the core is included in an amount from about 5 to about 20 percent, preferably from about 6 to about 10 percent, most preferably about 8 percent by weight of the core. In terms of whole tablet weight (e.g., core plus compression coating), the one or more disintegrant(s) in the core are included in an amount from about 0.1 to about 5 percent, preferably from about 0.3 to about 2 percent, by weight of the tablet (entire formulation).

According to the present invention, the core containing active drug is completely surrounded or substantially surrounded by a compression coating. The compression coating preferably delays the release of the pharmaceutically active agent for a predetermined period of time, which time is dependent upon the formulation of the coating and the thickness of the coating layer. The appropriate time period for the release of the active ingredient can be determined prior to the preparation of the formulation, and the formulation can be designed by applying the appropriate thickness and composition of the coating to achieve the desired time delay prior to release of the active ingredient and the desired release rate of the active ingredient following the time delay.

Preferably, the compression coating comprises a natural or synthetic gum which can function as a gelling agent, causing the core to be surrounded by the gel when the compression coated tablet is exposed to an environmental fluid (e.g., water or gastrointestinal fluid) and thereby causing the drug to be released after diffusion of the environmental fluid through the compression coating, the dissolution of the drug into the environmental fluid, and the egress of the dissolved drug into the fluid surrounding the compression coated tablet.

In certain embodiments, gums for use in the compression coating include, for example and without limitation, heteropolysaccharides such as xanthan gum(s), homopolysaccharides such as locust bean gum, galactans, mannans, vegetable gums such as alginates, gum karaya, pectin, agar, tragacanth, accacia, carrageenan, tragacanth, chitosan, agar, alginic acid, other polysaccharide gums (e.g. hydrocolloids), and mixtures of any of the foregoing. Further examples of specific gums which may be useful in the compression coatings of the invention include, but are not limited to, acacia catechu, salai guggal, indian bodellum, copaiba gum, asafetida, cambi gum, Enterolobium cyclocarpum, mastic gum, benzoin gum, sandarac, gambier gum, butea frondosa (Flame of Forest Gum), myrrh, konjak mannan, guar gum, welan gum, gellan gum, tara gum, locust bean gum, carageenan gum, glucomannan, galactan gum, sodium alginate, tragacanth, chitosan, xanthan gum, deacetylated xanthan gum, pectin, sodium polypectate, gluten, karaya gum, tamarind gum, ghatti gum, Accaroid/Yacca/Red gum, dammar gum, juniper gum, ester gum, ipil-ipil seed gum, gum talha (acacia seyal), and cultured plant cell gums including those of the plants of the genera: acacia, actinidia, aptenia, carbobrotus, chickorium, cucumis, glycine, hibiscus, hordeum, letuca, lycopersicon, malus, medicago, mesembryanthemum, oryza, panicum, phalaris, phleum, poliathus, polycarbophil, sida, solanum, trifolium, trigonella, *Afzelia africana* seed gum, *Treculia africana* gum, detarium gum, cassia gum, carob gum, *Prosopis africana* gum, *Colocassia esulenta* gum, *Hakea gibbosa* gum, khaya gum, scleroglucan, zea, mixtures of any of the foregoing and the like.

In certain especially preferred embodiments, the compression coating comprises a heteropolysaccharide such as xanthan gum, a homopolysaccharide such as locust bean gum, or a mixture of one or more hetero- and one or more homopolysaccharide(s). Heterodisperse excipients, previously disclosed as a sustained release tablet matrix in bur U.S. Pat. Nos. 4,994,276, 5,128,143, and 5,135,757, may be utilized in the compression coatings of the present invention. For example, in certain embodiments of the present invention, a gelling agent of both hetero- and homo-polysaccharides which exhibit synergism, e.g., the combination of two or more polysaccharide gums producing a higher viscosity and faster hydration than that which would be expected by either of the gums alone, the resultant gel being faster-forming and more rigid, may be used in the compression coatings of the present invention.

The term "heteropolysaccharide" as used in the present invention is defined as a water-soluble polysaccharide containing two or more kinds of sugar units, the heteropolysaccharide having a branched or helical configuration, and having excellent water-wicking properties and immense thickening properties.

An especially preferred heteropolysaccharide is xanthan gum, which is a high molecular weight ($>10^6$) heteropolysaccharide. Other preferred heteropolysaccharides include derivatives of xanthan gum, such as deacylated xanthan gum, the carboxymethyl ether, and the propylene glycol ester.

The homopolysaccharide materials used in the present invention that are capable of cross-linking with the heteropolysaccharide include the galactomannans, i.e., polysaccharides that are composed solely of mannose and galactose. A possible mechanism for the interaction between the galactomannan and the heteropolysaccharide involves the interaction between the helical regions of the heteropolysaccharide and the unsubstituted mannose regions of the galactomannan. Galactomannans that have higher proportions of unsubstituted mannose regions have been found to achieve more interaction with the heteropolysaccharide. Hence, locust bean gum, which has a higher ratio of mannose to galactose, is especially preferred as compared to other galactomannans, such as guar and hydroxypropyl guar.

In certain preferred embodiments, the heteropolysaccharide comprises from about 1 to about 50 percent and the homopolysaccharide material comprises from about 50 to about 1 percent by weight of the compression coating. In certain preferred embodiments, the ratio of heteropolysaccharide to homopolysaccharide material is from about 1:3 to 3:1, preferably from about 2:3 to 3:2, or 1:1.

In a certain preferred embodiment, the compression coating comprises from about 5 to about 70 percent or more by weight of a hydrophilic material (e.g., gums). In certain preferred embodiments of the present invention, the higher the percentage of gums in the compression coating, the longer the delay of the release or "lag time" of the active agent.

In certain embodiments, the percent of gums in the compression coating corresponds to a delayed release of the active agent which is independent of pH. For example, in certain preferred embodiments, when the compression coating is less than about 25% gums, preferably comprising about 5 to about 15% gums, the delayed release is more independent of pH than a compression coating comprising greater than about 25% gums (e.g., 30, 40, or 50% gums).

In certain preferred embodiments, the compression coating also includes pharmaceutically acceptable excipients, for example, a saccharide such as a monosaccharide, a disaccharide or a polyhydric alcohol, and/or mixtures of any of the foregoing, or microcrystalline cellulose or a starch. Examples of suitable such excipients include sucrose, dextrose, lactose, fructose, xylitol, sorbitol, mannitol, starches, mixtures thereof and the like. In certain embodiments, it is preferred that a soluble pharmaceutical excipient such as lactose, dextrose, sucrose, mannitol, or mixtures thereof is included in the materials to be used in the compression coating. In certain preferred embodiments, the gum(s) is wet granulated with the pharmaceutically acceptable excipient prior to its use as a compression coating on the surface of the inner cores of the invention. The compression coating may comprise, e.g., up to about 95% pharmaceutically acceptable excipient(s), by weight.

In certain embodiments, the amount of gum(s) contained in the compression coating is from about 1 percent to about 90 percent by weight, preferably from about 6.5 percent to about 83 percent of the total tablet, by weight.

In certain embodiments, it is possible to dry mix the ingredients of the compression (delayed release) coating without utilizing a wet granulation step. If the mixture is to be manufactured without a wet granulation step, and the final mixture is to be compression coated onto a pre-formed tablet core, it is preferred that all or part of the pharmaceutically acceptable excipient(s) should impart sufficient compressibility to, provide a pharmaceutically acceptable product. The properties and characteristics of a specific excipient system prepared according to the present invention may be dependent in part on the individual characteristics, e.g., of the homo- and heteropolysaccharide constituents, in terms of polymer solubility, glass transition temperatures etc., as well as on the synergism both between different homo- and heteropolysaccharides and between the homo- and heteropolysaccharides and the inert saccharide constituent(s) in modifying dissolution fluid-excipient interactions.

In certain embodiments of the invention where the compression coating comprises a heteropolysaccharide, a homopolysaccharide, or both, a release-modifying agent as described in our previous patents directed to the use of these materials in sustained release matrices can also be utilized in the compression coating. Such release-modifying agents and pre-manufactured excipients disclosed in our U.S. Pat. Nos. 5,455,046; 5,512,297; 5,554,387; 5,667,801; 5,846,563; 5,773,025; 6,048,548; 5,662,933; 5,958,456; 5,472,711; 5,670,168; and 6,039,980 may be utilized in the compression coatings of the present invention.

Thus, for example, the release-modifying agent may comprise an ionizable gel-strength enhancing agent. The ionizable gel strength-enhancing agent that is optionally used in conjunction with the present invention may be monovalent or multivalent metal cations. The preferred salts are the inorganic salts, including various alkali metal and/or alkaline earth metal sulfates, chlorides, borates, bromides, citrates, acetates, lactates, etc. Specific examples of suitable ionizable gel strength enhancing agent include calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride. Multivalent metal cations may also be utilized. However, the preferred ionizable gel strength-enhancing agents are bivalent. Particularly preferred salts are calcium sulfate and sodium chloride. The ionizable gel strength enhancing agents of the present invention are added in an amount effective to obtain a desirable increased gel strength due to the cross-linking of the gelling agent (e.g., the heteropolysaccharide and homopolysaccharide gums). In alternate embodiments, the ionizable gel strength-enhancing agent is included in the delayed release excipient of the present invention in an amount from about 1 to about 20% by weight of the delayed release excipient, and in an amount 0.5% to about 16% by weight of the final dosage form. In certain embodiments, the inclusion of an ionizable gel strength-enhancing agent not only delays the release of the active, but also provides for a sustained release of the active agent.

In certain embodiments of the present invention, the (delayed release) compression coating coated onto the core comprises from about 1 to about 90 percent by weight of a gelling agent comprising a heteropolysaccharide gum and a homopolysaccharide gum, from about 0 to about 20 percent by weight of an ionizable gel strength enhancing agent, and from about 10 to about 95 percent by weight of an pharmaceutically acceptable excipient. In other embodiments, the compression coating material, comprises from about 5 to about 75 percent gelling agent (gum), from about 0 to about 15 percent ionizable gel strength enhancing agent, and from about 30 to about 95 percent pharmaceutically acceptable excipient (e.g., an inert diluent). In yet other embodiments, the compression coating material comprises from about 7.5 to about 50 percent gelling agent, from about 0 to about 10 percent ionizable gel strength enhancing agent, and from about 30 to about 95 percent pharmaceutically acceptable excipient.

Surfactants that may be used in the present invention generally include pharmaceutically acceptable anionic surfactants, cationic surfactants, amphoteric (amphipathic/amphophilic) surfactants, and non-ionic surfactants. Suitable pharmaceutically acceptable anionic surfactants include, for example, monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates (including sodium lauryl sulfate (SLS)), ethoxylated alkyl sulfates, ester linked sulfonates (including docusate sodium or dioctyl sodium succinate (DSS)), alpha olefin sulfonates, and phosphated ethoxylated alcohols.

Suitable pharmaceutically acceptable cationic surfactants include, for example, monoalkyl quaternary ammonium salts, dialkyl quaternary ammonium compounds, amidoamines, and aminimides.

Suitable pharmaceutically acceptable amphoteric (amphipathic/amphophilic) surfactants, include, for example, N-substituted alkyl amides, N-alkyl betaines, sulfobetaines, and N-alkyl β-aminoproprionates.

Other suitable surfactants for use in conjunction with the present invention include polyethyleneglycols as esters or ethers. Examples include polyethoxylated castor oil, polyethoxylated hydrogenated castor oil, polyethoxylated fatty acid from castor oil or polyethoxylated fatty acid from hydrogenated castor oil. Commercially available surfactants that can be used are known under trade names Cremophor, Myrj, Polyoxyl 40 stearate, Emerest 2675, Lipal 395 and PEG 3350.

Other release-modifying pharmaceutically acceptable agents that may be added in appropriate quantities for their particular ability to modify dissolution rates include, for example: stearic acid, metallic stearates, stearyl alcohol, hydrogenated cotton seed oil, sodium chloride and certain disintegrants that are described below.

The quantity of such release-modifying agent employed depends on the release characteristics required and the nature of the agent. For a delayed release formulation according to the invention, the level of release-modifying agents used may be from about 0.1 to about 25%, preferably from about 0.5 to about 10% by weight of the total composition.

In certain other embodiments of the invention, the compression coating includes a pH-modifying agent. The pH-modifying agent may be present in the compression coating from about 1% to about 10% by weight of the final dosage form. In preferred embodiments, the pH-modifying agent is an organic acid such as citric acid, succinic acid, fumaric acid, malic acid, maleic acid, glutaric acid or lactic acid.

In certain preferred embodiments, the release of drug occurs when aqueous environmental fluid (e.g., water or gastrointestinal fluid, etc. surrounding the dosage form) diffuses through the compression coating of the dosage form, resulting in hydration of the core and dissolving the drug, which then can pass into the fluid surrounding the core.

In certain preferred embodiments, the delayed release of the drug (lag time) is varied by increasing the thickness of the compression coating (increased lag time) or by decreasing the thickness of the compressing coating (decreased lag time). The delayed release may also be varied, e.g., by changing the gum(s) included in the delayed release compression coating, selecting a particular combination of gums, by including or not including a pharmaceutically acceptable excipient, such as a saccharide (including polysaccharides) or a combination of saccharide(s) (or polysaccharides) in the compression coating, by changing or by adding additional agents to the compression coating which cause the compression coating to further delay the diffusion of water (or gastrointestinal fluid) through the compression coating (e.g., matrix) into the inner core (thereby allowing hydration of the inner core). In addition, the compression force used to apply the compression coating may be used to alter the release rate of the active ingredient. Also, release can be modified via the use of an extragranular excipient addition to the compression coating. Such ingredients may comprise, for example, microcrystalline cellulose, polyvinylpyrrolidone, polyethylene glycol, and the like.

The delayed release of the drug may further be varied by utilizing a further coating (i) between the core and the compression coating; (ii) over the compression coating; or (iii) both between the core and the compression coating and over the compression coating. Such coatings may comprise, for example a hydrophilic polymer (such as hydroxypropylmethylcellulose) and/or a hydrophobic polymer (such as an acrylic polymer, a copolymer of acrylic and methacrylic acid esters, an alkylcellulose such as ethylcellulose, etc.). In such circumstances, the release of drug from the dosage form may not only be occurring as fluid diffuses through the compression coating; erosion of the further coatings described in this paragraph may also delay the release of drug.

The dissolution rates of the present invention (with or without the optional release modifying agents mentioned above) may be further modified by incorporation of a hydrophobic material in the compression coating, which slows the hydration of the gums without disrupting the hydrophilic matrix. This is accomplished in alternate embodiments of the present invention by granulating the delayed release excipient with a solution or dispersion of a hydrophobic material prior to the compression coating of the core. The hydrophobic polymer may be selected from an alkylcellulose such as ethylcellulose, other hydrophobic cellulosic materials, polymers or copolymers derived from acrylic or methacrylic acid esters, copolymers of acrylic and methacrylic acid esters, zein, waxes, shellac, hydrogenated vegetable oils, and any other pharmaceutically acceptable hydrophobic material known to those skilled in the art. The solvent for the hydrophobic material may be an aqueous or organic solvent, or mixtures thereof. The amount of hydrophobic material incorporated into the delayed release excipient is that which is effective to slow the hydration of the gums without disrupting the hydrophilic matrix formed upon exposure to an environmental fluid. In certain preferred embodiments of the present invention, the hydrophobic material is included in the compression coating in an amount from about 1 to about 20 percent by weight.

The compression coating may also contain suitable quantities of, e.g., lubricants, binders, granulating aids, diluents, colorants, flavorants and glidants which are described hereinafter and are which are conventional in the pharmaceutical art.

In preferred embodiments where the materials to be included in the compression coating are pre-manufactured, the combination of the gum gelling agent (e.g., a mixture of xanthan gum and locust bean gum) with the pharmaceutical excipient(s), with or without a release modifying agent, provides a ready-to-use compression coating product in which a formulator need only apply the material onto the core by compression coating to provide the desired chronotherapeutic dosage forms. The compression coating may comprise a physical admix of the gums along with a soluble excipient such as compressible sucrose, lactose, dextrose, etc., although it is preferred to granulate or agglomerate the gums with a plain pharmaceutically acceptable excipient (i.e., crystalline) sucrose, lactose, dextrose, mannitol, etc., to form a delayed release excipient for use in the compression coating. The granulate form has certain advantages including the fact that it can be optimized for flow and compressibility.

The gums and optional pharmaceutical excipients used in the compression coating are preferably prepared according to any agglomeration technique to yield an acceptable excipient product. In wet granulation techniques, the desired amounts of the hydrophilic material (e.g., heteropolysaccharide gum and/or the homopolysaccharide gum) and the inert diluent are mixed together and thereafter a moistening agent such as water, propylene glycol glycerol, alcohol or the like is added to prepare a moistened mass. Next, the moistened mass is dried. The dried mass is then milled with conventional equipment into granules. Thereafter, the excipient product is ready to use.

The (preferably) pre-manufactured delayed release excipient is preferably free-flowing and directly compressible. Accordingly, the excipient may be directly compressed onto a pre-formed inner core of a therapeutically active medicament to form coated tablets. The delayed release coating mixture, in an amount sufficient to make a uniform coating onto a preformed tablet core, is subjected to tableting in a conventional production scale tableting machine at normal compression pressure, i.e., about 2000-1600 lbs/sq in. However, the mixture should not be compressed to such a degree that there is subsequent difficulty in its hydration when exposed to gastric fluid.

The average particle size of the granulated delayed release excipient of the present invention ranges from about 50 microns to about 400 microns and preferably from about 185 microns to about 265 microns. The particle size of the granulation is not narrowly critical, the important parameter being that the average particle size of the granules must permit the formation of a directly compressible excipient which forms a coating over pharmaceutically active tablet cores. The desired tap and bulk densities of the granulation of the present invention are normally between from about 0.3 to about 0.8 g/ml, with an average density of from about 0.5 to about 0.7 g/ml.

The compression coatings of the present invention preferably have uniform packing characteristics over a range of different particle size distributions and are capable of processing onto the pre-formed tablet core using direct compression, following the addition of a lubricant.

In addition to being (optionally) used in the tablet core, in certain embodiments it is preferred that one or more pharmaceutically acceptable lubricants be added to the compression coating materials (preferably pre-agglomerated) prior to the mixture being compression coated onto the surface of the core. Examples of suitable lubricants for use in the core and compression coating of the invention include, for example and without limitation, talc, stearic acid, vegetable oil, calcium stearate, zinc stearate, magnesium stearate, etc. Preferably, an effective amount of any generally accepted pharmaceutical lubricant, including calcium or magnesium soaps is preferably added to the mixture of ingredients prior to compression of the mixture onto the solid preformed tablet core. An especially preferred lubricant is sodium stearyl fumarate, NF, commercially available under the trade name Pruv® from JRS Pharma LP.

In certain embodiments, the present invention is further directed towards a method of manufacturing the delayed release solid oral dosage forms (e.g., tablets) of the present invention. In certain preferred embodiments, the steps for preparation of a delayed release oral solid dosage form of the present invention may include the following:

Preparation of inner core formulation:
1. (A) Wet granulate active ingredient (e.g., drug) together with the pharmaceutically acceptable surfactant and optional excipients, followed by drying and milling as necessary to obtain a granulate; or
   (B) Dry blend the active together with the pharmaceutically acceptable surfactant and optional excipients using geometric dilution as necessary to obtain a granulate;
2. Optionally, extragranularly add excipients to the material prepared in Step 1 with appropriate blending;
3. Preferably, lubricate powder blend prepared in Step 1 or 2:
4. Compress core using powder blend prepared in Step 3 with an appropriate press.
5. Optionally, applying a functional film coating onto the tablet cores prepared in Step 4;

Preparation of delayed release (compression) coating may be accomplished, e.g., as follows:
6. (A) Wet granulate a gum(s) (e.g., a heteropolysaccharide gum and a homopolysaccharide gum) together with optional excipients to form a delayed release material (agglomerated particles), and then dry the delayed release material; or
   (B) Dry blend a gum(s) together with optional excipients to form a delayed release material (granulate);
7. Preferably, mill the delayed release material prepared in Step 6;
8. Preferably, lubricate the delayed release material prepared in Step 6 or 7; Coating of inner core:
9. Compression coat the delayed release material prepared in Steps 6-8 over the tablet cores' prepared in Step 1-5;
10. Optionally, film coat the final dosage form (if desired).

In certain embodiments, steps 4 & 10 are combined in a single unit operation when using e.g., a Dry-Cota Press as described hereinafter. A functional coating of the tablet cores may be possible using the Dry-Cota Press if a modification is made to the press to add a core tablet feeder system.

A Manesty Dry-Cota press consists of two side by side interconnected tablet presses where the core is made on one press then mechanically transferred to the next press for compression coating. Each "press" has an independent powder feed mechanism so that core blend is loaded on one machine and coating blend on the other. Mechanical transfer arms rotate between the machines to remove cores from one press and transfer them to the coating press. Other and more modern types of presses which may be used (e.g. Elizabeth Hata HT-AP44-MSU-C, Killian RLUD, Fette PT 4090) have a dual feed system for coating blend and pre-made cores. This configuration is more flexible, in that cores can be pan coated with a functional or cosmetic coating before compression coating. In addition, this allows multiple compression coating-layers to be achieved by recycling tablets that have already been compression coated. Both types of presses have mechanisms to center the tablet within the coating both vertically and radially. One of ordinary skill would understand that other tablet presses may be used to provide for the final dosage forms of the present invention.

Although typically the compression coating surrounds the entire core, in certain embodiments of the present invention, the compression coating substantially surrounds, but does not entirely surround the tablet core. In such instances, the release of drug from the tablet core will occur first from that portion of the inner core to which the compression is not applied. In other embodiments of the invention, compression coating is not applied to the same thickness around the entire inner core, thereby creating areas of the compressed dosage form that release drug earlier (and later) than other areas. This may be accomplished, e.g, by having the core to which the compression coating is applied not being centered in the press.

For best results, the tablets formed from the compression coating of the core are from about 4 to about 25 kP, preferably about 5 to about 15 kP, most preferably about 8 to about 9 kP hardness. In certain preferred embodiments, for round compression coated tablets the diameter may be up to ⅝ inch or greater, and for caplet shaped compression coated tablets the diameter may be up to ¾ inch or greater. The average flow of the (non-compression) coatings prepared in accordance with the present invention is from about 25 to about 40 g/sec.

In certain embodiments of the present invention, the compression coated tablet may then be further overcoated with an enteric coating material or a hydrophobic material. Examples of suitable enteric polymers include cellulose acetate phthalate, hydroxypropyl-methylcellulose phthalate, polyvinylacetate phthalate, methacrylic acid copolymer, shellac, hydroxypropylmethylcellulose succinate, cellulose acetate, trimellitate, and mixtures of any of the foregoing. An example of a suitable commercially available enteric material is available under the trade name Eudragit® L30D55.

In further embodiments, the dosage form may be coating with a hydrophilic coating in addition to or instead of the above-mentioned enteric coating or hydrophobic coating. An example of a suitable material that may be used for such a hydrophilic coating is hydroxypropylmethylcellulose (e.g., Opadry®, commercially available from Colorcon, West Point, Pa.).

In still further embodiments, the optional enteric and/or hydrophobic and/or hydrophilic coatings may be alternatively or additionally applied as an intermediate layer(s) between the core and the compression coating.

The optional enteric and/or hydrophobic and/or hydrophilic coatings may be applied in any pharmaceutically acceptable manner known to those skilled in the art. For example, in one embodiment, the coating is applied via a fluidized bed or in a coating pan. For example, the coated tablets may be dried, e.g., at about 60-70° C. for about 3-4 hours in a coating pan. The solvent for the hydrophobic polymer or enteric coating may be organic, aqueous, or a mixture of an organic and an aqueous solvent. The organic solvents may be, e.g., isopropyl alcohols ethanol, and the like, with or without water.

In additional embodiments of the present invention, a support platform is applied to the tablets manufactured in accordance with the present invention. Suitable support platforms are well known to those skilled in the art. An example of suitable support platforms is set forth, e.g., in U.S. Pat. No. 4,839,177, hereby incorporated by reference. In that patent, the support platform partially coats the tablet, and consists of a polymeric material insoluble in aqueous liquids. The support platform may, for example, be designed to maintain its impermeability characteristics during the transfer of the therapeutically active medicament. The support platform may be applied to the tablets, e.g., via compression coating onto part of the tablet surface, by spray coating the polymeric materials comprising the support platform onto all or part of the tablet surface, or by immersing the tablets in a solution of the polymeric materials.

The support platform may have a thickness of, e.g., about 2 mm if applied by compression, and about 10µ if applied via spray-coating or immersion-coating. Generally, in embodiments of the invention wherein a hydrophobic polymer or enteric coating is applied to the tablets over the delayed release coating, the tablets are coated to a weight gain from about 1 to about 20%, and in certain embodiments preferably from about 5% to about 10%.

Materials useful in the hydrophobic coatings and support platforms of the present invention include derivatives of acrylic acid (such as esters of acrylic acid, methacrylic acid, and copolymers thereof) celluloses and derivatives thereof (such as ethylcellulose), polyvinylalcohols, and the like.

As mentioned above, the cores and/or compression coatings may also contain suitable quantities of, e.g., lubricants, binders, granulating aids, diluents, colorants, flavorants and glidants which are conventional in the pharmaceutical art.

Examples of suitable binders for use in the present invention include for example and without limitation, povidone, polyvinylpyrrolidone, xanthan gum, cellulose gums such as carboxymethylcellulose, methyl cellulose, hydroxypropylmethylcellulose, hydroxycellulose, gelatin, starch, and pregelatinized starch.

Examples of suitable glidants for use in the present invention include talc, silicon dioxide, and cornstarch.

In certain embodiments of the present invention, the tablet core includes an additional dose of the drug (or a therapeutically effective dose of a different drug) included in either the (optional) hydrophobic or enteric coating, or in an additional (optional) overcoating coated on the outer surface of the tablet core (without the hydrophobic or enteric coating) or as an additional coating layer coated on the surface of the base coating(s) comprising the compression coating and, if applicable, hydrophobic and/or enteric coating material. This may be desired when, for example, a loading dose of the drug is needed to provide therapeutically effective blood levels of the active agent when the formulation is first exposed to gastric fluid. The loading dose of drug included in the coating layer may be, e.g., from about 10% to about 40% of the total amount of drug included in the formulation.

Examples of drugs that are suitable for incorporation in the present invention include:
antihistamines (e.g., azatadine maleate, brompheniramine maleate, carbinoxamine maleate, chlorpheniramine maleate, dexchlorpheniramine maleate, diphenhydramine hydrochloride, doxylamine succinate, methdilazine hydrochloride, promethazine, trimeprazine tartrate, tripelennamine citrate, tripelennamine hydrochloride and triprolidine hydrochloride);
antibiotics (e.g., penicillin V potassium, cloxacillin sodium, dicloxacillin sodium, nafcillin sodium, oxacillin sodium, carbenicillin indanyl sodium, oxytetracycline hydrochloride, tetracycline hydrochloride, clindamycin phosphate, clindamycin hydrochloride, clindamycin palmitate HCL, lincomycin HCL, novobiocin sodium, nitrofurantoin sodium, metronidazole hydrochloride); antituberculosis agents (e.g., isoniazid);
cholinergic agents (e.g., ambenonium chloride, bethanecol chloride, neostigmine bromide, pyridostigmine bromide);
antimuscarinics (e.g., anisotropine mbethylbromide, clidinium bromide, dicyclomine hydrochloride, glycopyrrolate, hexocyclium methylsulfate, homatropine methylbromide, hyoscyamine sulfate, methantheline bromide, hyoscine hydrobromide, oxyphenonium bromide, propantheline bromide, tridihexethyl chloride);

sympathomimetics (e.g., bitolterol mesylate, ephedrine, ephedrine hydrochloride, ephedrine sulphate, orciprenaline sulphate, phenylpropanolamine hydrochloride, pseudoephedrine hydrochloride, ritodrine hydrochloride, salbutamol sulphate, terbutaline sulphate);

sympatholytic agents (e.g., phenoxybenzamine hydrochloride); miscellaneous autonomic drugs (e.g., nicotine);

iron preparations (e.g., ferrous gluconate, ferrous sulphate);

haemostatics (e.g., aminocaproic acid);

cardiac drugs (e.g., acebutolol hydrochloride, disopyramide phosphate, flecainide acetate, procainamide hydrochloride, propranolol hydrochloride, quinidine gluconate, timolol maleate, tocamide hydrochloride, verapamil hydrochloride);

antihypertensive agents (e.g., captopril, clonidine hydrochloride, hydralazine hydrochloride, mecamylamine hydrochloride, metoprolol tartrate); vasodilators (e.g., papaverine hydrochloride);

non-steroidal anti-inflammatory agents (e.g., choline salicylate, ibuprofen, ketoprofen, magnesium salicylate, meclofenamate sodium, naproxen sodium, tolmetin sodium);

opiate agonists (e.g., codeine hydrochloride, codeine phosphate, codeine sulphate, dextromoramide tartrate, hydrocodone bitartrate, hydromorphone hydrochloride, pethidine hydrochloride, methadone hydrochloride, morphine sulphate, morphine acetate, morphine lactate, morphine meconate, morphine nitrate, morphine monobasic phosphate, morphine tartrate, morphine valerate, morphine hydrobromide, morphine hydrochloride, propoxyphene hydrochloride);

anticonvulsants (e.g., phenobarbital sodium, phenyloin sodium, troxidone, ethosuximide, valproate sodium);

tranquilizers (e.g., acetophenazine maleate, chlorpromazine hydrochloride, fluphenazine hydrochloride, prochlorperazine edisylate, promethazine hydrochloride, thioridazine hydrochloride, trifluoroperazine hydrochloride, lithium citrate, molindone hydrochloride, thiothixine hydrochloride);

chemotherapeutic agents (e.g., doxorubicin, cisplatin, floxuridine, methotrexate, combinations thereof, etc.);

lipid lowering agents (e.g., gemfibrozil, clofibrate, HMG-CoA reductase inhibitors, such as for example atorvastatin, cerivastatin, fluvastatin, lovastatin, pravastatin, simvastatin, etc.);

$H_2$-antagonists (e.g., cimetidine, famotidine, nizatidine, ranitidine HCl, etc.);

anti-coagulant and anti-platelet agents (e.g., warfarin, cipyridamole, ticlopidine, etc.);

bronchodilators (e.g., albuterol, isoproterenol, metaproterenol, terbutaline, etc.);

stimulants (e.g., benzamphetamine hydrochloride, dextroamphetamine sulphate, dextroamphetamine phosphate, diethylpropion hydrochloride, fenfluramine hydrochloride, methamphetamine hydrochloride, methylphenidate hydrochloride, phendimetrazine tartrate, phenmetrazine hydrochloride, caffeine citrate);

barbiturates (e.g., amylobarbital sodium, butabarbital sodium, secobarbital sodium);

sedatives (e.g., hydroxyzine hydrochloride, methprylon); expectorants (e.g., potassium iodide);

antiemetics (e.g., benzaquinamide hydrochloride, metoclopropamide hydrochloride, trimethobenzamide hydrochloride);

gastro-intestinal drugs (e.g., ranitidine hydrochloride); heavy metal antagonists (e.g., penicillamine, penicillamine hydrochloride);

antithyroid agents (e.g., methimazole);

genitourinary smooth muscle relaxants (e.g., flavoxate hydrochloride, oxybutynin hydrochloride);

vitamins (e.g., thiamine hydrochloride, ascorbic acid);

unclassified agents (e.g., amantadine hydrochloride, colchicine etidronate disodium, leucovorin calcium, methylene blue, potassium chloride, pralidoxime chloride.

steroids, particularly glucocorticoids (e.g., prednisolone, prednisone, cortisone, hydrocortisone, methylprednisolone, betamethasone, dexamethasone, triamcinolone).

The drugs may be in their base for, or a pharmaceutically acceptable salt or complex may be used. The list of possible therapeutic classes and particular drugs listed above are representative only, and are not meant to limit the scope of the invention in any way.

The chronotherapeutic formulations of the present invention may be utilized to treat any condition known (or which become known) to those skilled in the art which would benefit from such therapy. These therapies include, but are not limited to allergic rhinitis, attention deficit disorder asthma, arthritis, cancer therapy, cardiovascular disease, high cholesterol, hypertension, and ulcers.

With respect to allergic rhinitis, major symptoms of sneezing, runny nose and stuffy nose are typically worse upon rising than during the middle of the activity span of a given day. The chronotherapeutic approach of the present invention could also help offset the sneezing, nasal congestion and runny nose and eyes that come with allergies. For instance, hay fever symptoms peak in the morning. Some studies show taking an antihistamine in the evening, rather than during the day, helps block symptoms before a patient gets out of bed, rather than waiting for symptoms to begin. Thus, it would be greatly desirable to provide a chronotherapeutic oral formulation of, for e.g., an antihistamine, which would be taken at a convenient time and which would have release the dose at a time point such that the maximal effect of the dosage form is reached in the morning.

With respect to asthma, normal lung function undergoes circadian changes and reaches a low point in the early morning hours. This dip particularly pronounced in people with asthma. Chronotherapy for asthma is aimed at getting maximal effect from bronchodilator medications during the early morning hours. It has been proferred that the key to managing asthma cases is chronotherapy, and that treatment to improve nighttime asthma will allow for improvement of daytime manifestations of asthma. Certainly dosage and timing are related for asthma patients, whose number has doubled since 1975 in America alone. The majority of asthma patients suffer most at night, possibly because that is when cortisol, the body's natural anti-inflammatory, is at its lowest level. The most common time for an attack is 4 am, so the agony of the asthma itself is often compounded by the further strain of sleeplessness. Thus, it would be greatly desirable to provide a chronotherapeutic oral formulation of, e.g., an antihistamine, which would be taken at a convenient time and which would release the dose at, e.g., just before 4 a.m., such that the maximal effect of the dosage form is reached at that time.

The chronotherapeutic formulations of the invention may also be used to treat arthritis. Glucocorticosteroids have a very favourable effect on the symptoms of rheumatoid arthritis, e.g. morning stiffness, joint pain and joint swelling. With respect to arthritis, chronobiological patterns have been observed with arthritis pain. People with osteoarthritis (the most common form of arthritis) tend to have less pain in the morning and more at night. But for people with rheumatoid arthritis, the pain usually peaks in the morning and decreases as the day wears on. Recent animal studies showing that joint inflammation in rats fluctuates over a 24-hour period support these observations by both patients and physicians. Potential drug candidates in this therapeutic area include (for all forms of arthritis) standard treatment, NSAIDs and corticosteroids, etc. Preferably, the dosages should be timed to ensure that the highest blood levels of the drug coincide with peak pain. For osteoarthritis—the optimal time for an NSAID (ibuprofen, etc.) would be around noon or mid-afternoon. For rheumatoid arthritis—the optimal time for an NSAID to be taken is after the evening meal.

Glucocorticoids for use in the present invention include for example, prednisolone, prednisone, cortisone, hydrocortisone, methylprednisolone, betamethasone, dexamethasone, triamcinolone, mixtures thereof, and pharmaceutically acceptable salts thereof. Prednisone is particularly preferred. Prednisone is a potent pharmaceutical agent which has been commercially available for many years. Prednisone is characterized by pronounced anti-inflammatory activity, when administered locally or systemically. Prednisone is known as an anti-inflammatory and anti-rheumatic drug. Preferably, when the active agent is prednisone, the prednisone is in an amount of from about 0.1 to about 20 mg, preferably from about 1 to about 6 mg, and in most preferred embodiments about 1, 2, 5, 7.5 or 10 mg.

Equivalent doses of other glucocorticoids can be calculated based on the following chart:

| Glucocorticoid | Approximate Equivalent Dose (mg) |
|---|---|
| Cortisone | 25 |
| Hydrocortisone | 20 |
| Prednisone | 5 |
| Prednisolone | 5 |
| Triamcinolone | 4 |
| Methylprednisolone | 4 |
| Dexamethasone | 0.75 |
| Betamethasone | 0.6-0.75 |

With respect to attention deficit disorder, it has been observed that peak plasma concentrations of the drug are lower when sustained release formulations are used, and in some instances, sustained release formulations of methylphenidate have been shown to have lower efficacy than conventional dosage forms. A dosage form which provides for a delay in release of maximally effective amount of an agent to treat attention deficit disorder could be useful, particularly if the dosage form provides in one administration, and initial release of the active agent, followed by a predictable delay and then a second release of the active agent. Potential drug candidates include stimulants such as for example methylphenidate and pharmaceutically acceptable salts thereof.

With respect to cancer therapy, animal studies suggest that chemotherapy may be more effective and less toxic if cancer drugs are administered at carefully selected times. The studies currently suggest that there may be different chronobiological cycles for normal cells and tumor cells. If this is true, the goal would be to time the administration of cancer drugs to the chronobiological cycles of tumor cells, making them more effective against the cancer and less toxic to normal tissues. Potential drug candidates include, e.g., injectables such as doxorubicin and cisplatin (combination) and floxuridine.

Chronotherapeutics are not entirely new in the treatment of cardiovascular disease. Since 1986, people with angina have been treated with nitroglycerin patches that are attached to their chest or shoulder in the morning and are removed in the evening. This is considered to be "side door" chronotherapy because it is not based on the recognition that a disease gets worse at a certain time of the day, and therefore should be treated at that time of the day. Rather, it arose out of the recognition that nitroglycerin is not effective when it is continuously administered. Based on the fact that cardiologic diseases have a 24-hour pattern, the use of the chronotherapeutic formulations of the present invention would be greatly desirable. It has been thought by those skilled in the art that heart attacks, sudden death, angina and stroke all seem to peak in the morning hours. Thus, it would be greatly desirable to provide a chronotherapeutic oral formulation which would be taken at a convenient time and which would release the dose such that the maximal effect of the dosage form is reached at that time. Potential drug candidates include antihypertensive agents, antiischemic agents, and agents that control clotting.

With respect to hypertension, blood pressure fluctuates over the 24-hour (circadian) period. In most normotensive patients and in most patients with essential hypertension (systemic vasoconstriction is associated with increased peripheral vascular resistance in arterioles), circadian mechanisms plus differences in activity and stress during the sleep/activity cycle cause blood pressure to rise rapidly upon awakening. After it peaks during daytime activity, blood pressure declines during sleep by 10% to 20% of the mean daytime level. Both blood pressure and heart rate typically rise early in the morning and significantly increase myocardial oxygen demand to cause myocardial ischemia in patients with known or nondiagnosed coronary artery disease. The rapid surge in blood pressure on awakening is associated with an increased incidence of morning cerebrovascular accidents and myocardial infarction. Moreover, the incidence of cerebrovascular accidents and other cardiovascular events (sudden death, acute myocardial infarction, and total ischemic burden) also follows a circadian pattern, being greatest during the first 6 hours of the activity span (6 a.m. to 12 noon) and least during sleep, as observed from the Framingham Study results. Morning surges of blood pressure can theoretically rupture atherosclerotic plaques in coronary arteries, injure underlying tissue, and promote clot formation in the early morning when coagulation processes are most active. Thus, it would be greatly desirable to provide a chronotherapeutic oral formulation which would be taken at a convenient time and which would have release the dose such that the maximal effect of the dosage form is reached at that time.

In addition to a rapid rise in blood pressure on awakening a "dip" in blood pressure occurs in most people during nighttime sleep. The dip may vary or be absent in patients with more severe forms of hypertension and among patients with secondary hypertension, in whom blood pressure either fails to decline as expected or else rises during sleep, relative to daytime levels. Blood pressure patterns have been grouped into four categories: (i) "dippers" show a 10% to 20% decline in blood pressure during nighttime sleep compared with their average daytime blood pressure level; (ii) "nondippers" have nighttime blood pressures that vary little from the daytime levels; (iii) "superdippers" show a decline in blood pressure greater than 20% at night from the daytime mean level; and (iv) "risers" experience a high blood pressure at night compared with daytime levels. Deviations in blood pressure from normal circadian patterns are associated with an increased risk of end-organ damage and adverse cardiovascular events. Hypertensive patients with nocturnal patterns of superdipping or nondipping blood pressure are more likely to develop eye, renal, and cardiac pathologies and show a higher rate of cardiovascular events, such as cerebrovasculazr accidents and myocardial infarction, than normal dippers.

Chronotherapy is a treatment approach that allows for better control of blood pressure during the day and night by delivering medication in amounts proportional to patients' needs and, therefore, in synchrony with the circadian blood pressure rhythm. More chronotherapeutic antihypertension medication is delivered in the morning and daytime when blood pressure is greatest, and less at night when blood pressure typically declines to the lowest level. The incidence of early morning cardiovascular events could theoretically be decreased if early morning surges in blood pressure and heart rate are blunted by the chronotherapeutic administration of indicated drugs using appropriate delivery systems.

The calcium channel blocker verapamil reduces heart rate as well as blood pressure, which is especially beneficial for patients with both ischemic heart disease and hypertension. These characteristics of verapamil and its appropriate anrtihy-life made it a good choice for the formulation of an anrtihypertensive drug with a chronotherapeutic oral drug absorption system (CODAS). This system was designed to be taken at bedtime, to cause a 4- to 5-hour initial lag in drug delivery and, thereafter, to achieve a controlled release of drug. CODAS-verapamil capsules (Verelan® PM) were made using the CODAS multiparticulate technology along with verapamil-coated beads. When taken as directed, this formulation results in a maximum verapamil plasma concentration around the time of awakening in the morning. Studies showed that nighttime dosing of verapamil chronotherapy allows for better control of the sharp morning blood pressure rise than do conventional antihypertensive medications. Bedtime dosing with verapamil chronotherapy also controls daytime blood pressure without inducing hypotension or superdipping of blood pressure at night, reducing the risk of target organ damage due to poor perfusion pressure. Furthermore, verapamil chronotherapy is designed to deliver more medication in the daytime than conventional verapamil and other antihypertension medications. Potential drug candidates include antihypertensive medications such as calcium channel blockers.

Medications to control high cholesterol, such as HMG-CoA reductase inhibitors, are also considered to work better when given in the evening, a time when enzyme activity levels peak. Therefore, it would be greatly desirable to provide a chronotherapeutic oral formulation which would be taken at a convenient time and which would have release the dose such that the maximal effect of the dosage form is reached at that time.

Treating ulcers is another example where timing is important. Since it is known that the acidity produced by the stomach peaks at 6 p.m., medication to reduce the secretion of acid in the stomach can therefore be delivered accordingly.

The benefits of chronotherapeutics include safety and more efficient treatment than conventional therapies. This is achieved by delivering more medication when risk of disease is greater, and delivering less medication when potential for disease symptoms are less likely. Other benefits to the patient include an increased quality of life and a once-a-day drug delivery system to increase patient compliance.

In certain preferred embodiments of the invention where the manifestations of the disease state to be treated (e.g., asthmatic attack, pain from arthritis) are greatest upon awakening, the chronotherapeutic formulations are preferably orally administered to the patient at bedtime (e.g., at about 9 or 10 p.m.) and have a lag time of about 5 or 6 hours, so that, e.g., a substantial portion of the drug in the compression coated delayed release oral dosage form is released, e.g., between 2-3 a.m., or between 3-4 a.m., and the drug is absorbed from the gastrointestinal tract and provides therapeutic efficacy at a time which correlates with the peak of the manifestations of the disease state.

In situations where the active agent is a low dose active agent (e.g., a drug administered in a (unit) dose amount from about 0.01 mg to about 40 mg), in certain preferred embodiments; the total tablet weight is from about 220 mg to about 900 mg; and the core weight is preferably from about 56 mg to about 170 mg. Preferably, the core is from about 5 to about 23 percent, most preferably about 18 to about 20 percent by weight of the total tablet weight. In embodiments wherein the active agent is a low dose active agent, the coating is preferably from about 150 mg to about 850 mg. Preferably, the coating is from about 75 to about 94 percent by weight, most preferably from about 78 to 80 percent by weight of the total tablet. Preferably, where the active dose is a low dose active agent, the ratio of the core to gum (in the compression coating) is from about 1:0.37 to about 1:5, preferably from about 1:0.37 to about 1:1.12, most preferably from about 1:0.75. Where the active dose is a low dose active agent, the ratio of the core to compression coating material (all ingredients) is preferably from about 1:2 to about 1:9, and in certain embodiments more preferably about 1:4.

In situations where the active agent is a relatively high dose active agent (e.g., a drug administered in a (unit) dose amount from about 41 mg to about 300 mg), the ratio of core to gum (in the compression coating) is from about 1:0.3 to about 1:3, preferably from about 1:0.6 to about 1:1.5. In certain embodiments, preferably where the active agent is a high dose active agent, the ratio of the core to compression coating material (all ingredients) is from about 1:1 to about 1:5, preferably from about 1:2 to about 1:3. In situations where the active agent is a relatively high dose active agent, the total tablet weight is preferably from about 500 mg to about 1500 mg, more preferably from about 750 mg to about 1000 mg.

In the appended examples, the cores comprising the active agent are typically compression coated with the coating formulation by hand on a rotary tablet press. In such a process, roughly half the outer core material is first added to the die. An inner core tablet is typically centered on the powder bed and is covered with the other half of the outer coating powder. However, one skilled in the art will appreciate that compression coating may be accomplished via automated tablet presses for commercialization. Prior to compression coating with any tablet press, preferably 0.75% Pruv® (sodium stearyl fumarate, NF) or another suitable lubricant is added to the compression coating material(s). In certain examples wherein the coatings are indicate by the gums, for example, 50% xanthan gum (XG), the coating comprises 50% xanthan gum diluted with dextrose; and for example 50% locust bean gum (LBG), the coating comprises 50% locust bean gum diluted with dextrose, etc.

DETAILED DESCRIPTION OF THE PREFERRED EMBODIMENTS

The following examples illustrate various aspects of the present invention. They are not to be construed to limit the claims in any manner whatsoever.

EXAMPLE 1

A delayed release material to be used in the compression coatings of the invention is prepared having the following formulation listed in Table 1:

TABLE 1

| Component | Percentage |
|---|---|
| 1. Xanthan Gum | 3 |
| 2. Locust Bean Gum | 4.5 |
| 3. Mannitol | 92.5 |
| 4. Water* | q.s. (20-40) |

*Removed during processing

The process for the preparation of the delayed release material is as follows:

Process:
1. The requisite amounts of xanthan gum, locust bean gum, and mannitol are dry blended in a high speed mixer/granulator for 3 minutes.
2. Water is added to the dry blended mixture, and granulated for another 3 minutes.
3. The granulation is then dried in a fluid bed dryer to a LOD (loss on drying) of less than about 10% by weight (e.g., 4-7% LOD).

EXAMPLE 2

A delayed release material to be used in the compression coatings of the invention is prepared having the formulation listed in Table 2:

TABLE 2

| Component | Percentage |
|---|---|
| 1. Xanthan Gum | 6 |
| 2. Locust Bean Gum | 9 |
| 3. Mannitol | 85 |
| 4. Water* | q.s. (20-40) |

*Removed during processing

Process:
The same process for Example 1 is used to prepare the delayed release material of Example 2 to be used in the compression coatings of the invention.

EXAMPLE 3

A delayed release material to be used in the compression coatings of the invention is prepared having the formulation listed in Table 3:

TABLE 3

| Component | Percentage |
|---|---|
| 1. Xanthan Gum | 20 |
| 2. Locust Bean Gum | 30 |
| 3. Mannitol | 50 |
| 4. Water* | q.s. (20-40) |

*Removed during processing

Process:
The same process for Example 1 is used to prepare the delayed release material of Example 3 to be used in the compression coatings of the invention.

EXAMPLE 4

A prednisone core composition was prepared having the ingredients set forth in Table 4:

TABLE 4

| Component | Percent | amt. (mg/tab) |
|---|---|---|
| 1. Prednisone, USP | 11.7 | 7.5 |
| 2. Prosolv*90M | 67.0 | 42.9 |
| 3. Syloid** | 0.5 | 0.3 |
| 4. Talc | 3.8 | 2.4 |
| 5. Samarium Oxide*** | 9.4 | 6.0 |
| 6. Polyethylene Glycol 3350 | N/A | N/A |
| 7. Sodium Lauryl Sulfate | N/A | N/A |
| 8. Sodium Croscarmellose**** | 1.9 | 1.2 |
| 9. Explotab***** | 5.6 | 3.6 |
| 10. Sodium Stearyl Fumarate | 0.2 | 0.1 |
| Total weight | | 64.0 |

*Prosolv is a commercially available (from JRS Pharma) augmented microcrystalline cellulose.
**Syloid is a commercially available colloidal silicon dioxide.
***Samarium oxide is included in the cores in order to perform scintigraphic data analysis. It is understood that the formulations of the examples are meant to encompass cores that do not include samarium oxide.
****sodium croscarmellose is a disintegrant.
*****sodium starch glycolate is commercially available (from JRS Pharma LP) as Explotab The core composition of Example 4 was prepared using the following process.

Process:
1. Dispense (1), (2), (3) and (5) into V-Blender and blend for 10 minutes.
2. Dispense (8) and (9) into V-Blender and blend for 5 minutes.
3. Dispense (4) into V-Blender and blend for 5 minutes.
4. Dispense (6) and/or (7) into V-Blender (if applicable) and blend for 5 minutes
5. Dispense (10) into V-Blender and blend for 5 minutes.
6. Compress into tablets using 3/16" S.C. round beveled edge tooling.

EXAMPLE 5

A prednisone core composition including PEG (polyethylene glycol) was prepared having the ingredients set forth in Table 5:

TABLE 5

| Component | Percent | amt. (mg/tab) |
|---|---|---|
| 1. Prednisone, USP | 11.7 | 7.5 |
| 2. Prosolv 90M | 38.9 | 24.9 |
| 3. Syloid | 0.5 | 0.3 |
| 4. Talc | 3.8 | 2.4 |
| 5. Samarium Oxide | 9.4 | 6.0 |
| 6. Polyethylene Glycol 3350 | 28.1 | 18.0 |
| 7. Sodium Lauryl Sulfate | N/A | N/A |
| 8. Sodium Croscarmellose | 1.9 | 1.2 |
| 9. Explotab | 5.6 | 3.6 |
| 10. Sodium Stearyl Fumarate | 0.2 | 0.1 |
| Total weight | | 64.0 |

Process:
The same process used to prepare the core composition of Example 4 was used to prepare the core composition of Example 5.

EXAMPLE 6

A prednisone core composition including SLS (sodium lauryl sulfate) and PEG (polyethylene glycol) was prepared having the ingredients set forth in Table 6:

TABLE 6

| Component | Percent | Amt. (mg/tab) |
|---|---|---|
| 1. Prednisone, USP | 11.7 | 7.5 |
| 2. Prosolv 90M | 45.5 | 29.1 |
| 3. Syloid | 0.5 | 0.3 |
| 4. Talc | 3.8 | 2.4 |
| 5. Samarium Oxide | 9.4 | 6.0 |
| 6. Polyethylene Glycol 3350 | 18.8 | 12.0 |
| 7. Sodium Lauryl Sulfate | 2.8 | 1.8 |
| 8. Sodium Croscarmellose | 1.9 | 1.2 |
| 9. Explotab | 5.6 | 3.6 |
| 10. Sodium Stearyl Fumarate | 0.2 | 0.1 |
| Total weight | | 64.0 |

Process:

The same process used to prepare the core composition of Example 4 was used to prepare the core composition of Example 6.

EXAMPLES 7-9

In Examples 7-9, prednisone tablets were prepared having a core formulation of Example 5 and coatings as listed Table 7 below:

TABLE 7

| | Ex. 7 | | Ex. 8 | | Ex. 9 | |
|---|---|---|---|---|---|---|
| Component | % | mg/tab | % | mg/tab | % | mg/tab |
| 1. Core of Ex. 5 | 20.4 | 64.0 | 20.4 | 64.0 | 20.4 | 64.0 |
| 2. Delayed Release material of Ex. 1 | 79.0 | 248.0 | N/A | N/A | N/A | N/A |
| 3. Delayed Release material of Ex. 2 | N/A | N/A | 79.0 | 248.0 | N/A | N/A |
| 4. Delayed Release material of Ex. 3 | N/A | N/A | N/A | N/A | 79.0 | 248.0 |
| 5. Sodium Stearyl Fumarate | 0.6 | 2.0 | 0.6 | 2.0 | 0.6 | 2.0 |
| Tablet weight (mg) | | 314.0 | | 314.0 | | 314.0 |
| Hardness (Kp) | | 12.0 | | 12.0 | | 12.0 |

Process:
1. Dispense appropriate delayed release material from Example 1 12 or 3, (numbers 2, 3, or 4 in above Table 7) and sodium stearyl fumarate (5) into V-Blender and blend for 5 minutes.
2. Set up tablet press with 5/16" S.C. round beveled edge tooling.
3. Dispense approximately 125 mg of the delayed release blend into the 5/16" die (lower layer) and smooth level the blend with a spatula.
4. Place the here core (1) in the center of the die on to of the bottom layer.
5. Dispense approximately 125 mg of the appropriate delayed release blend into the 5/16" die (upper layer) and smooth and level the blend with a spatula.
6. Compress the Lower Layer, Inner core and Upper Layer into a tablet.

The tablets of Examples 7-9 were tested using USP apparatus type III with 250 mL solution (pH 1.5) at 15 dips per minute (dpm) giving the following results listed in Table 8:

TABLE 8

| Time (hours) | Example 7 | Example 8 | Example 9 |
|---|---|---|---|
| 0.0 | 0.0 | 0.0 | 0.0 |
| 2.0 | 96.9 | 0.0 | 0.0 |
| 3.0 | 98.3 | 0.0 | 0.0 |
| 4.0 | 98.6 | 51.7 | 0.0 |
| 5.0 | 98.7 | 69.3 | 0.0 |
| 6.0 | 98.7 | 97.3 | 0.0 |
| 7.0 | 98.7 | 97.8 | 0.0 |
| 8.0 | 98.7 | 97.8 | 0.8 |
| 12.0 | 98.7 | 97.8 | 15.4 |

The formulation of Example 7 (% Gums of 7.5%) released significantly faster than the formulations of Example 8 (% Gums of 15.0%), and Example 9 (% Gums of 50.0%). As the amount of gum content is increased in the compression coating, there's a corresponding increase in lag time.

EXAMPLES 10-12

In Examples 10-12, prednisone tablets were prepared having a core formulation and coatings as listed Table 9 below:

TABLE 9

| | Ex. 10 | | Ex. 11 | | Ex. 12 | |
|---|---|---|---|---|---|---|
| Component | % | mg/tab | % | mg/tab | % | mg/tab |
| 1. Core of Ex. 4 | 20.4 | 64.0 | N/A | N/A | N/A | N/A |
| 2. Core of Ex. 5 | N/A | N/A | 20.4 | 64.0 | N/A | N/A |
| 3. Core of Ex. 6 | N/A | N/A | N/A | N/A | 20.4 | 64.0 |
| 4. Delayed Release material of Ex. 2 | 79.0 | 248.0 | 79.0 | 248.0 | 79.0 | 248.0 |
| 5. Sodium Stearyl Fumarate | 0.6 | 2.0 | 0.6 | 2.0 | 0.6 | 2.0 |
| Tablet weight (mg) | | 314.0 | | 314.0 | | 314.0 |
| Hardness (Kp) | | 8.0 | | 8.0 | | 8.0 |

Process:
1. Dispense delayed release material from Ex. 2 (4) and sodium stearyl fumarate (5) into V-Blender and blend for 5 minutes.
2. Set up tablet press with 5/16" S.C. round beveled edge tooling.
3. Dispense approximately 125 mg of the delayed release blend into the 5/16" die (lower layer) and smooth level the blend with a spatula.
4. Place the Inner core (1) or (2) or (3) in the center of the die on top of the bottom layer.
5. Dispense approximately 125 mg of the delayed release blend into the 5/16" die (upper layer) and smooth and level the blend with a spatula.
6. Compress the Lower Layer, Inner core and Upper Layer into a tablet.

The tablets of Examples 10-12 were tested using USP apparatus type III with 250 mL solution pH 1.5 at 15 dips per minute (dpm) giving the following results listed in Table 10:

TABLE 10

| Time (hours) | Example 10 | Example 11 | Example 12 |
|---|---|---|---|
| 0.0 | 0.0 | 0.0 | 0.0 |
| 3.0 | 0.0 | 0.0 | 0.0 |
| 4.0 | 15.4 | 35.8 | 27.8 |
| 5.0 | 66.4 | 81.8 | 73.6 |

TABLE 10-continued

| Time (hours) | Example 10 | Example 11 | Example 12 |
|---|---|---|---|
| 6.0 | 93.8 | 96.8 | 104.1 |
| 7.0 | 102.8 | 97.1 | 104.1 |
| 8.0 | 103.0 | 97.1 | 104.1 |

Formulations of Example 11, and Example 12 with the surfactant(s) included in the core are slightly faster than the reference formulation of Example 10 without the surfactant in the core. The addition of surfactant slightly increases the dissolution profile.

EXAMPLE 13

Effect of Surfactants (Dispersing-Agents) Polyethylene Glycol 3350 (PEG 3350) Sodium Lauryl Sulfate (SLS) Bio-analysis In Example 13, a biostudy was done using formulations prepared in accordance with the present invention. The study was a cross over design study consisting of five study periods of approximately 36 hours duration. Study periods 1-4 were separated by a minimum period of 72 hours between dosing and study period 5 was administered at least 14 days after the previous study period. Healthy male volunteers aged. 18-65, with no history of adverse reaction to steroids, gastrointestinal diseases or gastrointestinal surgery other than appendicectomy were included in the biostudy. Scintigraphic images and blood samples were taken at intervals up to 24 hours after dosing to compare the transit and disintegration times of the formulation with the pharmacokinetic data. Ten subjects completed the study.

The study design was as follows:
1. Number of Subjects: 10
2. The Dosing Regimen was as follows:
   Regimen A=Formulation of Example 10 (7.5 mg Prednisone) administered at approximately 9:00 am—2 hours after a standard breakfast.
   Regimen B=Formulation of Example 11 (7.5 mg Prednisone) administered at approximately 9:00 am—2 hours after a standard breakfast.
   Regimen C=Formulation of Example 12 (7.5 mg Prednisone) administered at approximately 9:00 am—2 hours after a standard breakfast.
   Regimen D=Immediate release 7.5 mg Prednisone tablets USP administered at approximately 9:00 am—2 hours after a standard breakfast.
   Regimen E=Formulation of Example 11 (7.5 mg Prednisone) administered at approximately 10:30 am—2 hours after a standard evening meal.
3. The Parameters Observed were as follows:
   a. Scientigraphic data analysis: To record movement of tablet from stomach to intestine. Scintigraphic data were analysed to obtain: gastric emptying time; small intestinal transit time; ileocaecal junction (ICJ) arrival time; residence time in ICJ; anatomical location and time of initial and complete disintegration of tablet core.
   b. Pharmacokinetics data analysis: Pharmacokinetic data were analysed to obtain $C_{max}$, $t_{max}$, $t_{lag}$, $AUC_{0-24}$, $AUC_{0-\infty}$, $\lambda_z$, and $t\frac{1}{2}$.

The Scintigraphic Results were as follows:

The time of complete disintegration for the Formulation of Example 10 was later than that for the Formulation of Example 11 and Example 12. The majority of tablets of the Formulation of Example 10 disintegrated in the colon and for the tablets of the Formulation of Examples 11 and 12 the majority of tablets disintegrated in the small bowel. Table 11 below lists the tablet disintegration (hours post-dose) for Regimens A, B, and C, and Table 12 below lists the location of the tablet disintegration of Regimens A, B, and C.

TABLE 11

| | Tablet disintegration (hours post-dose) | | |
|---|---|---|---|
| Disintegration | Regimen A (Ex. 10, am) | Regimen B (CDS 11, am) | Regimen C (Ex. 12, am) |
| Initial | 4.91 ± 1.44 | 3.34 ± 0.89 | 3.10 ± 0.69 |
| Complete | 6.05 ± 3.31 | 3.71 ± 0.94 | 3.28 ± 0.71 |

TABLE 12

The location of tablet disintegration

| | Gastrointestinal tract region with number of subjects having release in the respective region | | | | | | | |
|---|---|---|---|---|---|---|---|---|
| | S | PSB | MSB | DSB | ICJ | AC | HF | TC | SF |
| Regimen A (Ex. 10, am) | | | | | | | | | |
| Initial disintegration | — | — | 1 | 2 | — | 1 | 4 | 2 | — |
| Complete disintegration | — | — | — | 3 | — | 1 | 2 | 3 | 1 |
| Regimen B (Ex. 11, am) | | | | | | | | | |
| Initial disintegration | — | — | 2 | 5 | 1 | 2 | — | — | — |
| Complete disintegration | — | — | — | 6 | — | 4 | — | — | — |
| Regimen C (Ex. 12, am) | | | | | | | | | |
| Initial disintegration | — | — | — | 6 | 2 | 1 | — | — | 1 |
| Complete disintegration | — | — | — | 5 | 2 | 2 | — | — | 1 |

S—stomach,
PSB—proximal small bowel,
MSB—mid small bowel,
DSB—distal small bowel,
ICJ—ileocaecal junction,
AC—ascending colon,
HF—hepatic flexure,
TC—transverse colon,
SF—splenic flexure The Pharmacokinetic results (mean values) of Regimens A, B, C, D, and E from the biostudy, are listed in Table 13 below:

TABLE 13

| Parameter | Regimen A (Ex. 10, am) | Regimen B (Ex. 11, am) | Regimen C (Ex. 12, am) | Regimen D (IR tablet, am) | Regimen E (Ex. 11, pm) |
|---|---|---|---|---|---|
| $C_{max}$ (ng/ml) | 48.82 ± 50.09 | 123.16 ± 64.38 | 109.14 ± 50.00 | 197.32 ± 30.95 | 174.53 ± 16.55 |
| $T_{max}$ (hours) | 6.00 | 4.50 | 4.75 | 1.00 | 3.50 |
| $T_{lag}$ (hours) | 3.75 | 3.00 | 3.50 | 0.50 | 3.00 |
| $AUC_{0-24}$ (ng · h/ml) | 293 ± 309 | 619 ± 367 | 563 ± 305 | 858 ± 148 | 883 ± 154 |

TABLE 13-continued

| Parameter | Regimen A (Ex. 10, am) | Regimen B (Ex. 11, am) | Regimen C (Ex. 12, am) | Regimen D (IR tablet, am) | Regimen E (Ex. 11, pm) |
|---|---|---|---|---|---|
| $AUC_{0-\infty}$ (ng · h/ml) | 575 ± 327 | 959 ± 294 | 708 ± 392 | 1005 ± 39 | 923 ± 156 |
| $t_{1/2}$ (hours) | 3.37 ± 0.60 | 3.17 ± 0.14 | 3.40 ± 0.72 | 3.39 ± 0.01 | 3.58 ± 0.89 |

The delay in complete tablet disintegration for Regimen A compared with Regimens B and C is reflected in the slightly higher $T_{max}$ and the lower $C_{max}$ values for Regimen A than for Regimens B and C. The $AUC_{0-24}$ values of prednisolone were lower for Regimen A compared with Regimens B and C. Compared with the IR tablets the $C_{max}$ and $AUC_{0-24}$ values of prednisolone were approximately 33% lower for Regimen B and 39% lower for Regimen C. The $C_{max}$ and $AUC_{0-24}$ values for the formulation of Example 11 administered in the evening were approximately 1.4-fold higher than those values for the formulation of Example 11 administered in the morning.

The addition of a dispersing agent (e.g., a surfactant) resulted in significant increases in $C_{max}$ and AUC.

Night time dosing resulted in higher $C_{max}$ and AUC values with less variability. These values compare better to the IR product than Regimen A, B, C.

CONCLUSION

For the delayed release delivery systems administered in the morning, the time of complete disintegration was later for the formulation of Example 10 than for the formulations of Examples 11 and 12. Disintegration of the formulations of Examples 11 and 12 occurred higher in the gastrointestinal tract than the formulation of Example 10. In the majority of subjects disintegration of the formulation of Example 10 occurred in the colon and disintegration of the formulations of Example 11 and 12 occurred in the small intestine. The pharmacokinetic parameters for the three systems reflect these differences in disintegration with the rate and extent of absorption for prednisolone higher for the formulations of Example 11 and 12 than for Example 10, and $T_{max}$ and $T_{lag}$ occurring later for Example 10 than for Examples 11 and 12. Compared with the immediate release tablet formulation the rate and extent of absorption were lower for the delayed release delivery systems. Administration of Example 11 in the evening resulted in a higher rate and extent of absorption of prednisolone than administration of Example 11 in the morning.

The examples provided above are not meant to be exclusive. Many other variations of the present invention would be obvious to those skilled in the art, and are contemplated to be within the scope of the appended claims.

What is claimed is:

1. A delayed release oral solid dosage form comprising:
a tablet core comprising a mixture of a therapeutically effective amount of a drug and a pharmaceutically acceptable surfactant selected from the group consisting of (i) an anionic surfactant selected from the group consisting of monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates, ethoxylated alkyl sulfates, ester linked sulfonates, alpha olefin sulfonates, phosphated ethoxylated alcohols and mixtures thereof; (ii) a cationic surfactant selected from the group consisting of monoalkyl quaternary ammonium salts, dialkyl quaternary ammonium compounds, amidoamines, and aminimides, and mixtures thereof; (iii) an amphoteric surfactant selected from the group consisting of N-substituted alkyl amides, N-alkyl betaines, sulfobetaines, N-alkyl 6-aminoproprionates, and mixtures thereof; (iv) a polyethylene glycol, a polyethyleneglycol ester, a polyethyleneglycol ether, and mixtures thereof; and (v) a mixture of any of (i)-(iv); the surfactant comprising about 2.8 or from about 5 to about 50% of the core, by weight; and a delayed release material compression coated onto said core, said delayed release material comprising one or more natural or synthetic gums, said compression coating delaying the release of said drug from said dosage form until after a period of time from about 2 to about 18 hours after exposure of the dosage form to an aqueous solution; wherein the surfactant is included in an amount sufficient to facilitate the complete release of the drug from the dosage form in less than about 4 hours after initial release of the drug from the delayed release oral solid dosage form.

2. The delayed release oral solid dosage form of claim 1, wherein said surfactant is selected from the group consisting of an anionic surfactant, a cationic surfactant, an amphoteric surfactant, a non-ionic surfactant, and mixtures thereof.

3. The delayed release oral solid dosage form of claim 1, wherein said surfactant is in an amount of from about 5 to about 50 percent by weight of the core.

4. The delayed release oral solid dosage form of claim 1, wherein said drug is a glucocorticosteroid selected from the group consisting of prednisolone, prednisone, cortisone, hydrocortisone, methylprednisolone, betametasone, dexamethasone, triamcinolone, pharmaceutically acceptable salts thereof, and mixtures thereof.

5. The delayed release oral solid dosage form of claim 1, wherein said one or more natural or synthetic gums are agglomerated with a saccharide material prior to being compression coated onto said core.

6. The delayed release oral solid dosage form of claim 1, which delays release of said drug until at least about 4 hours to about 18 hours after exposure of the dosage form to an aqueous solution.

7. The delayed release oral solid dosage form of claim 1, wherein said delayed release material further comprises an ionizable gel strength enhancing agent selected from the group consisting of calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate, sodium fluoride, and mixtures thereof.

8. The delayed release oral solid dosage form of claim 1, wherein said core further comprises from about 5 to about 20 percent disintegrant, by weight.

9. The delayed release oral solid dosage form of claim 1, wherein said drug is a glucocorticosteroid.

10. The delayed release oral solid dosage form of claim 1, wherein said core further comprises an effective amount of disintegrant.

11. The delayed release oral solid dosage form of claim 1, wherein said gums comprise a mixture of xanthan gum and locust bean gum.

12. The delayed release oral solid dosage form of claim 1, wherein the drug and surfactant are granulated along with a disintegrant and a pharmaceutically acceptable inert diluent.

13. The delayed release oral solid dosage form of claim 1, wherein the surfactant is included in an amount sufficient to facilitate at least about 80% of the drug from the dosage form within about one hour after the initial release of the drug from the delayed release oral solid dosage form.

14. A delayed release oral solid dosage form comprising:
a core comprising a therapeutically effective amount of a drug, a pharmaceutically acceptable surfactant selected from a polyethylene glycol, a polyethyleneglycol ester, a polyethyleneglycol ether, and mixtures thereof, the surfactant comprising greater than 10 to about 50% of the core, by weight; and a delayed release material compression coated onto said core, said delayed release material comprising one or more natural or synthetic gums, said compression coating delaying the release of said drug from said dosage form until after a period of time from about 2 to about 18 hours after exposure of the dosage form to an aqueous solution; wherein the surfactant is included in an amount sufficient to facilitate the complete release of the drug from the dosage form in less than about 4 hours after initial release of the drug from the delayed release oral solid dosage form.

15. The delayed release oral solid dosage form of claim 14, wherein the drug and surfactant are granulated along with a disintegrant and a pharmaceutically acceptable inert diluent.

16. The delayed release oral solid dosage form of claim 14, wherein the core is a tablet core comprising a mixture of the drug and the surfactant.

17. The delayed release oral solid dosage form of claim 14, wherein the surfactant included in the core further comprises sodium lauryl sulfate.

18. The delayed release oral solid dosage form of claim 14, wherein the surfactant is included in an amount sufficient to facilitate at least about 80% of the drug from the dosage form within about one hour after the initial release of the drug from the delayed release oral solid dosage form.

19. The delayed release oral solid dosage form of claim 14, wherein the surfactant comprises from about 18.8% to about 28.1% polyethylene glycol.

20. The delayed release oral solid dosage form of claim 19, wherein the surfactant further comprises about 2.8% sodium lauryl sulfate.

\* \* \* \* \*